United States Patent [19]
Vara et al.

[11] Patent Number: 6,063,030
[45] Date of Patent: May 16, 2000

[54] PC BASED ULTRASOUND DEVICE WITH VIRTUAL CONTROL USER INTERFACE

[75] Inventors: Albert Vara, Coral Gables; William E. Glenn, Ft. Lauderdale; John W. Marcinka, Lighthouse Point; Robert L. Dhein, Ft. Lauderdale, all of Fla.

[73] Assignee: Adalberto Vara, Miami, Fla.

[21] Appl. No.: 09/124,172

[22] Filed: Jul. 28, 1998

Related U.S. Application Data

[63] Continuation-in-part of application No. 08/159,333, Nov. 29, 1993, abandoned.

[51] Int. Cl.[7] .................................................. A61B 8/00
[52] U.S. Cl. ........................................ 600/437; 600/440
[58] Field of Search ........................... 600/437, 440–447, 600/449; 73/625, 626, 620; 348/163

[56] References Cited

U.S. PATENT DOCUMENTS

| | | | |
|---|---|---|---|
| 4,227,417 | 10/1980 | Glenn | 73/625 |
| 4,246,791 | 1/1981 | Glenn | 73/620 |
| 4,248,090 | 2/1981 | Glenn | 72/620 |
| 4,257,271 | 3/1981 | Glenn | 73/626 |
| 4,317,370 | 3/1982 | Glenn | 73/620 |
| 4,509,526 | 4/1985 | Barnes et al. | 128/661.1 |
| 5,161,535 | 11/1992 | Short et al. | 128/660.01 |
| 5,315,999 | 5/1994 | Kinicki et al. | 128/660.07 |
| 5,379,771 | 1/1995 | Kawasaki et al. | 128/661.1 |
| 5,795,297 | 8/1998 | Daigle | 600/447 |

*Primary Examiner*—William E. Kamm
*Assistant Examiner*—Ali M Imam
*Attorney, Agent, or Firm*—Thomas R. Vigil

[57] ABSTRACT

The PC based ultrasound system utilizes a standard PC central processing unit or CPU (an Intel 486 processor or better), standard PC memory storage and retrieval components, a scan conversion board and a video processing board, all disposed and electronically linked to the bus in the computer. Additionally, the analog drive and return scan video signals are sent to and received from a video processing and motor control unit. The video processing and motor control unit is coupled to an ultrasound scan lead or probe. The virtual control user interface for the ultrasound system includes a software driven display obtained from memory. The software driven display reveals images representative of hardware control configurations for many different ultrasound processors. The images provided by the software driven display include: gain control tactile user interfaces, image enhancement control tactile user interfaces, focus control tactile user interface, multiple menu levels for gain control, image enhancement, and focus controls. In a further embodiment, the virtual control user interface is used in conjunction with a touch sensitive user input screen and the virtual control user interface includes a touch screen input command converter responsive to a user's touch on the touch sensitive display monitor to convert the tactile input into software commands. Other features include the ability to recall previously scanned ultrasound images, annotate recently acquired ultrasound images, preferably in color, electronically transfer the images to other peripheral computer equipment, and display a checklist for medical protocol involved in the ultrasound medical techniques. The medical protocol is loaded as pull down or pop up menu available to the user.

1 Claim, 22 Drawing Sheets

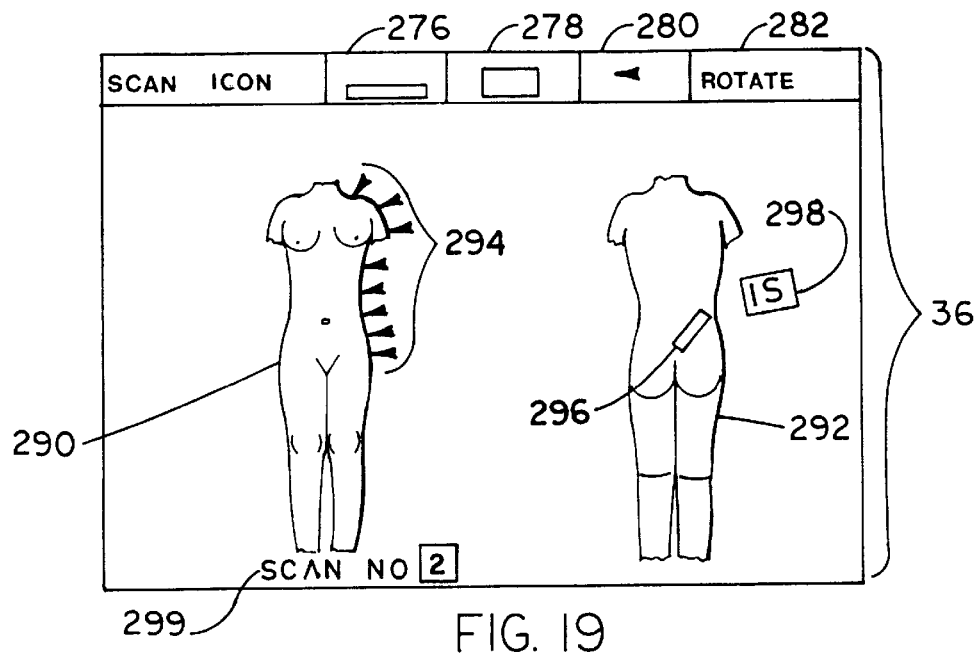
FIG. 19
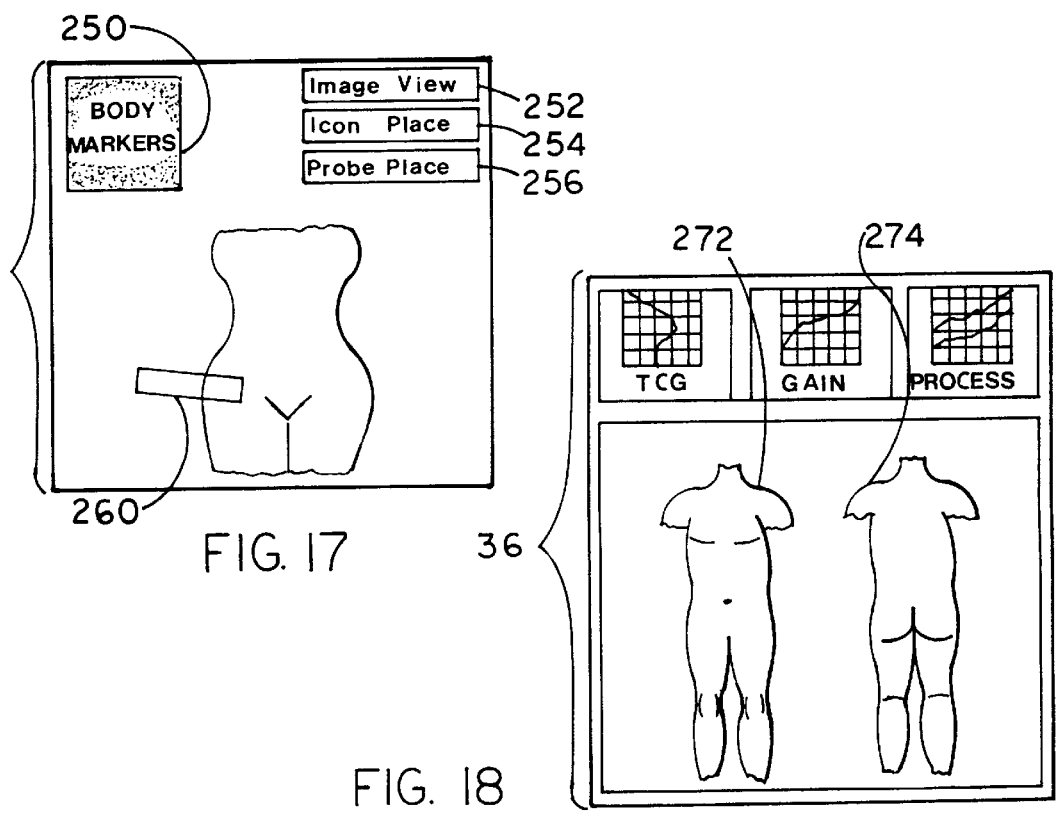
FIG. 17
FIG. 18

FIG. 24

| SUPER VISION | | PROBE ID | | | DATE | | |
|---|---|---|---|---|---|---|---|
| | | | | | SURNAME | | SEX |
| | | | | | FIRST INITIAL | | |
| | | | | | AGE | | |
| | | | | | PROCEDURE | | |

RENAL TRANSPLANT SCAN

USE 3.5 MHZ LINEAR ARRAY

OBTAIN MEASUREMENT OF L W AND D

SEND 3 FILMS TO DR POLLARD you have mail — 710

INFO — 34

Patient Information
Procedure Information
Protocol Information
Appointments
Measurements
Leave a Message
Supervision

FREEZE  SAVE  PHOTO

HELP AND COMMENTS A
HELP AND COMMENTS B

36

COLOR SCALE

GRAY SCALE

12

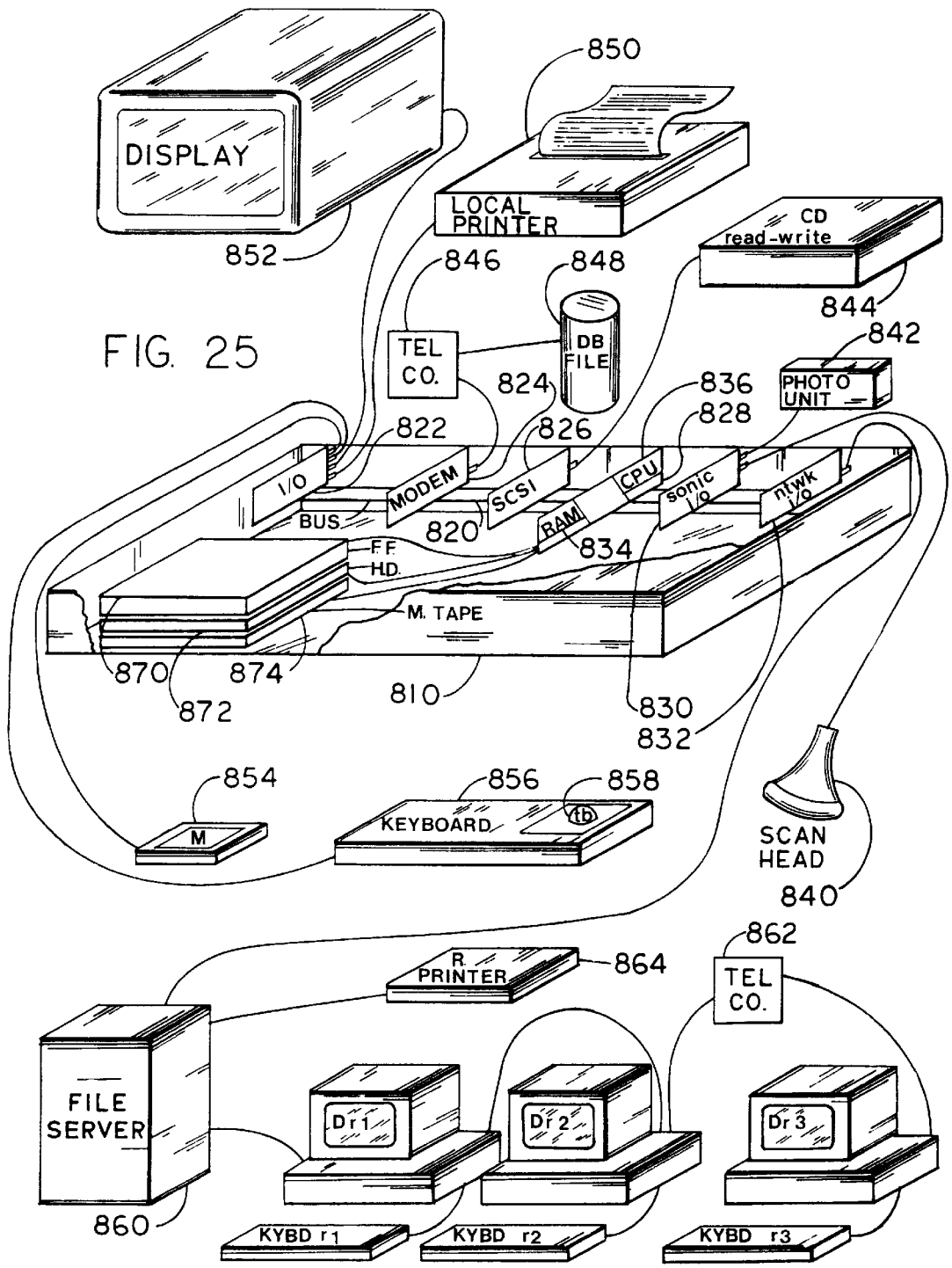

PC BASED ULTRASOUND DEVICE WITH VIRTUAL CONTROL USER INTERFACE

This is a continuation-in-part of U.s. application Ser. No. 08/159,333, filed Nov. 29, 1993, now abandoned.

TECHNICAL FIELD

The present invention relates to a personal computer or PC based ultrasound machine or device with a virtual control user interface. The PC based nature of the invention permits the user to change boards in the PC component box to, for example, upgrade his or her machine for use with a wider variety or different ultrasonic scan heads or probes. The user interface controls the ultrasound processor, driver and scan head. The invention also relates to a method which mimics the hardware configuration for other ultrasonic processors.

BACKGROUND ART

Ultrasound is utilized in many non-invasive medical procedures in order to detect and diagnosis a patient's condition. For example, ultrasonic scans are commonly used to detect and monitor the growth, viability and health of fetuses, to detect and assist in the diagnosis of liver, kidney, and other intestinal ailments, among others.

During these procedures, an ultrasound transducer head is placed atop or near the internal organ sought to be scanned. The ultrasonic image (generally resulting from the detection of sonic echoes by the ultrasonic transducer head) is displayed in essentially real time on a display monitor.

A significant number of ultrasound machines utilize user interfaces which are configured as knobs, slide switches, push buttons and other similar type tactile controls. The user must be trained to simultaneously hold the ultrasonic scan head on the body of the patient while adjusting the knobs, push buttons and slide controls on the ultrasound processor while further viewing the display monitor.

A difficulty arises when the physician or medical office wishes to upgrade the ultrasonic scan head or which is to replace or enhance the ultrasound processor unit electronically coupled to and driving the ultrasound scan head. In general, these ultrasound processor units were simply replaced with a larger enhanced model with a higher level of tactile control knobs, slide switches and push buttons. Of course, the number of tactile controls available to the user has a physical limitation in relation to the size of the overall processor unit. Further, the physician or medical office is required to train the user of the machine and the training is unique to a particular hardware and ultrasonic processing technique.

In the past, it has been necessary to purchase an entirely new ultrasound system if the physician wanted to upgrade his or her equipment. Prior art ultrasound systems normally did not permit upgrades by simply changing the boards internal to the machine casing. As a result, when technology made prior art systems obsolete, the physician was required to discard the entire machine, purchase a new machine and, more likely than not, learn to operate the new machine.

U.S. Pat. No. 4,227,417 to Glenn discloses an ultrasonic device with dynamic focussing of the ultrasonic transducer. U.S. Pat. No. 4,246,791 to Glenn discloses an ultrasound imaging system with a transducer, a variable delay circuit and a rotating mirror which directs the sonic pulses and echos to and from the transducer. U.S. Pat. No. 4,248,090 to Glenn discloses a rotating mirror in a scan or probe head. U.S. Pat. No. 4,257,271 to Glenn discloses an oscillating mirror in a scan head. U.S. Pat. No. 4,317,370 to Glenn discloses an ultrasound system with a single timing circuit which provides clocking signals to both the frame storage and the oscillatory mirror drive circuitry.

DISCLOSURE OF THE INVENTION

It is an object of the present invention to provide a PC based ultrasound system wherein the system can be upgraded or modified to accommodate new or different scan or probe heads simply by an exchange of a board within the PC casing.

It is an object of the present invention to provide a computer based virtual control user interface for an ultrasound processor and system.

It is a further object of the present invention to provide a virtual control user interface which incorporates multiple menu levels for the display of gain control images, ultrasound enhancement control images and focused controlled images.

It is a further object of the present invention to provide a virtual control user interface which can reveal images representative of hardware control configurations for a number of ultrasound processors.

It is an additional object of the present invention to provide a virtual control user interface which incorporates a touch screen display monitor.

It is another object of the present invention to provide a virtual control user interface which can be customized by the user to enhance the operability and effectiveness of the user interface.

It is a further object of the present invention to provide a virtual control - user interface which includes a pull down or pop up protocol check list or menu which may be used by the user to insure that the ultrasound techniques recorded by the ultrasound processor comply with a predetermined medical protocol.

It is another object of the present invention to provide an ultrasound processor which is configured with plug-in boards for a processor unit, input/output interface or display monitor, a keyboard, and various input/output interfaces for other peripheral computer equipment.

The PC based ultrasound system utilizes a standard PC central processing unit (an Intel 486 processor or better), standard PC memory storage and retrieval components, a scan conversion board and a video processing board, all disposed and electronically linked to the bus in the computer. Additionally, the analog drive and return scan video signals are sent to and received from a video processing and motor control unit. This unit is coupled to the scan head or probe. The virtual control user interface for an ultrasound processor includes a software driven display obtained from a memory unit in the ultrasound processor and displayed on a display monitor (part of the ultrasound processor) under control of a processor unit (which is also part of the ultrasound processor). The software driven display reveals images representative of hardware control configurations for other ultrasound processors. These ultrasound processors are electronically coupled to an ultrasound scan head via a scan head interface unit. The images provided by the software driven display and displayed by on the display include: a plurality of gain control tactile user interfaces, a plurality of ultrasound image enhancement control tactile user interfaces and, at least one focus control tactile user interface. The software driven display has multiple menu levels for the display of the gain control images, the ultrasound images enhancement control images and the focus control image. The software driven display is also further configured to reveal images of more than one ultrasound processor. In a further embodiment, the virtual control user interface is used in conjunction with a touch sensitive user input screen and the virtual control user interface includes a touch screen input command converter responsive to a users touch on the touch sensitive display monitor to convert the tactile input into a software command corresponding to the image proximally displayed on touch sensitive display monitor. Other features of the control user interface include the ability to recall previously scanned ultrasound images which are recorded in the memory unit of the ultrasound processor, to annotate recently acquired ultrasound images, preferably in color, such that the ultrasound electronic images and associated annotations can be electronically transferred from the ultrasound processor to other peripheral computer equipment, and a checklist for medical protocol involved in the ultrasound medical techniques. The medical protocol is loaded as pull down or pop up menu available to the user.

BRIEF DESCRIPTION OF THE DRAWINGS

Further objects and advantages of the present invention can be found in the detailed description of the preferred embodiments when taken in conjunction with the accompanying drawings in which:

FIG. 3A diagrammatically illustrates the timing gain control (TGC) user interface in one embodiment;

FIG. 11 diagrammatically illustrates another embodiment for the caliper or measurement control user interface;

FIG. 17, 18 and 19 diagrammatically illustrate the body marker or scan region menus and displays in accordance with the principles of the present invention;

FIGS. 22, 23 and 24 diagrammatically illustrate the system sub-menu, mode sub-menu and information sub-menu used in conjunction with one embodiment of the present invention;

FIG. 25 diagrammatically illustrates a system diagram for the ultrasound processor incorporating the virtual control user interface as well as that processor being electronically connected to various other computer elements. This figure also illustrates the interconnectivity of the ultrasound processor with these other computer peripheral elements;

BEST MODE FOR CARRYING OUT THE INVENTION

The present invention relates to a PC based ultrasound system and utilizes a standard PC central processing unit or CPU (an Intel 486 processor or better), standard PC memory storage and retrieval components, a scan conversion board and a video processing board, all disposed and electronically linked to the bus in the computer. Additionally, the analog drive and return scan video signals are sent to and received from a video processor and motor control unit which is currently external to the PC. This external unit is connected to the ultrasound scan head or probe. The invention also includes a virtual control user interface for the ultrasound processor and system, a method for establishing and using that virtual control user interface, an ultrasound processor having a high degree of interconnectivity with other computer peripheral equipment, and an ultrasound processor that is configured with plug-in electronic boards generally similar in nature to a personal computer.

Figure 1:
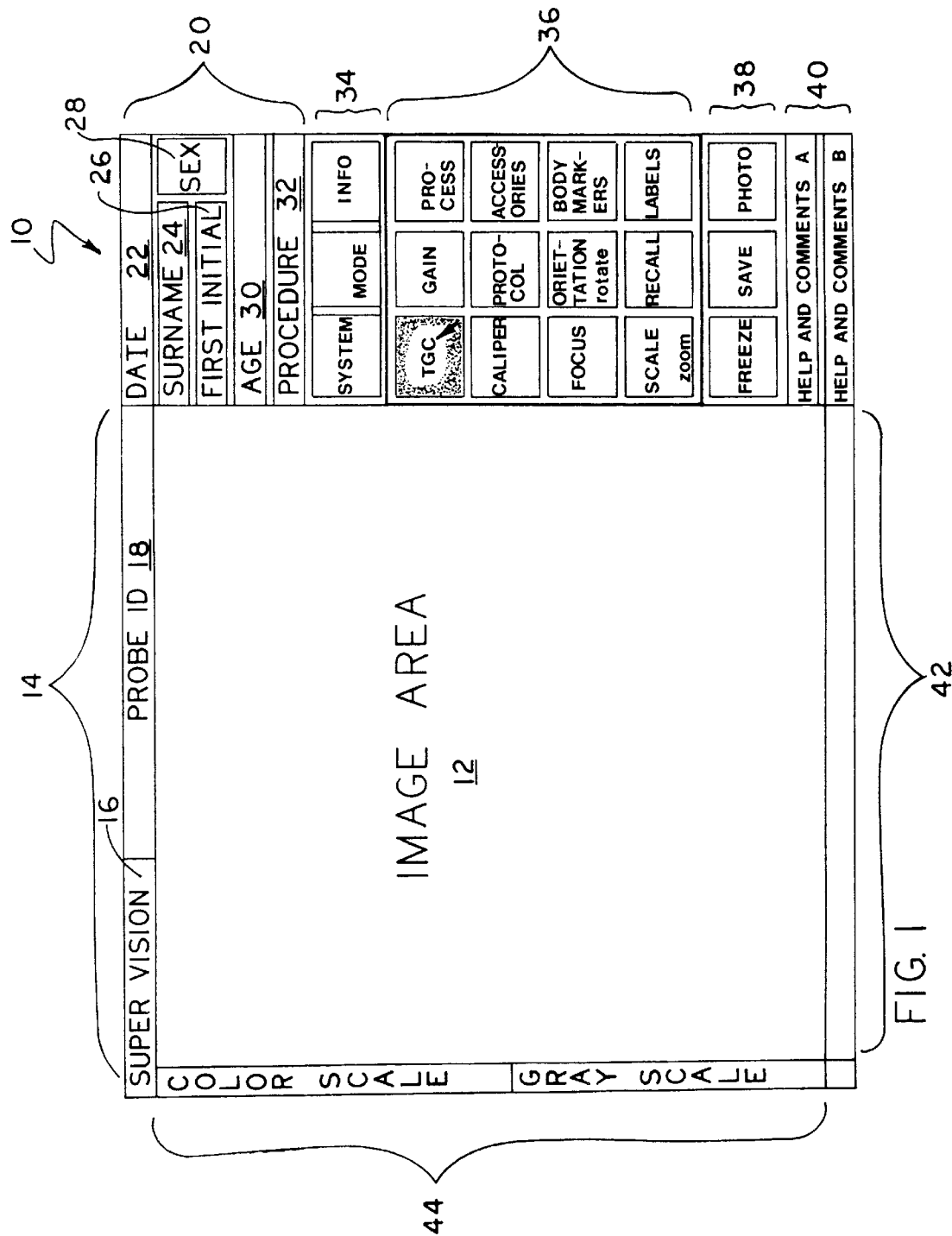
FIG. 1 diagrammatically illustrates one embodiment of the virtual control user interface main screen.

FIG. 1 diagrammatically illustrates one embodiment of the computer based virtual control user interface and particularly the main or primary menu display screen revealing the first electronic representation of a hardware control panel for another ultrasound processor. Main menu display screen 10 includes an ultrasound scan image area 12 (occupying approximately 60–80% of the display monitor) (see FIG. 25 and the accompanying explanatory text). The main menu display screen includes nine major regions one of which is the ultrasound scan image area 12. The second major region 14 is configured at the upper portions of the screen and includes a program identification area 16 (identify the program as SUPERVISION) and a probe identification or ultrasound scan head identification region 18. It should be noted that the present invention may be used in conjunction with several different types of ultrasound scan heads and therefore it may be important to display the type of scan head currently being utilized by the operator on a continuous basis during the ultrasound procedure. The upper menu region with software program area 16 and probe Id area 18 is generally displayed continuously.

The third screen region 20 includes a date display area 22, a surname or last name display area 24 (showing the last name of the patient currently being scanned by the user or operator of the ultrasound processor), the first initial of the person being scanned 26, the sex of the person being scanned at area 28, the age of the person being scanned at area 30, and a display region 32 showing the particular ultrasonic scanning procedure being carried out by the user on that patient. In general, the information in display screen region 20 is maintained throughout the ultrasound scan.

Display screen regions 34, 36 and 38 respectively reveal system or equipment configurations (area 34), a dynamic control menu screen region 36, and a critical function menu or screen region 38. The dynamic menu control panel 36 is primarily altered to reveal submenus and increasing detail of user actuatable controls during the operation of the virtual control user interface. However, other changes to the image screen area 12 as well the help and comment areas A B in screen region 40 are discussed in detail hereinafter.

The lower menu bar 42 has been left blank in the embodiment illustrated in FIG. 1. This area can be subject to future development and can be used to display prompts for function keys or other items which may assist the user in controlling the processing as well as the operation of the ultrasound scan head.

The last portion of the display screen 10 is the side bar menu display 44 which provides an indication to the user of the color selected on the display monitor as well as the intensity or gray scale of the image. The user can alter the gray scale and color scale of the ultrasound image in image area 12 in real time during an ultrasonic scan of a patient simply by touching the screen or pointing and actuating a mouse or track ball controlled curser/pointer in these screen regions.

Preferably, the screen display region 28 reveals a small image of a man or a woman rather than simply a designation of M for male or F for female.

As discussed in detail with respect to FIG. 25, the displays generally illustrated in FIGS. 1–24 are shown on a display monitor. The display monitor may be a common cathode ray tube or other display monitor customarily associated with computer equipment or may be more sophisticated touch screen monitor. As is known by persons of ordinary skill in the art, monitors are available that detect presence or absence of a user's finger on a certain portion of the screen. This type of display monitor is identified herein as a "touch screen display monitor." The touch screen display monitors are meant to cover devices that are capable of displaying various indicia and images as well as providing an input device for the user to select one or more control functions visually indicated on the display screen.

As discussed later in conjunction with FIG. 25, the user may select one or more elements or menu features from the main menu display screen 10 by use of a cursor directed by a mouse or track ball (as shown in FIG. 1 on the TGC control) or by use of the tab key or other key stroke combinations.

In any event, when the cursor falls within one of the operable menu blocks, principally display screen areas 34, 36 and 38, the particular element in that menu block lights up or is preliminarily activated such that the user has a visual indication of the precise location of the cursor. It should be noted that the particular menu and sub-menu for that function has not been activated until the user depresses the activation button on the mouse, track ball or strikes the enter or return key on the keyboard. For touch type screens, the user must strike the screen segment immediately proximate the displayed function. In another embodiment discussed in conjunction with FIG. 3B, the user can control a machine function by touching or moving the curser to a specific screen region not immediately proximate the display function.

In FIG. 1, the cursor has been positioned atop the TGC or time gain control of the ultrasound processor virtual control user interface. The TGC control is lit as shown by the illumination lines. When the cursor arrives at a certain menu block, help and comments area A (display screen area 40) indicates the english language equivalent for that command function. The Comment A Table, which is set forth below, provides exemplary comments which would appear in the upper portion of display screen area 40.

Comment A Table

| Cursor Position | Comment |
| --- | --- |
| TGC | Time Gain Control |
| Gain | Power-Gain-Reject |
| Process | Select Correct Process |
| Caliper | Measure Between Points |
| Access | Select Peripheral Accessories |
| Focus | Select Focal Points |
| Body | Id Scan Area on Body |
| Label | Annotate Image |

One important feature of the present invention is the ability of the virtual control user interface to display in the help and comment area 40 a foreign language equivalent for the TGC. Also, another important feature of the present invention enables the user to preset certain elements and textual explanatory material in help and comment area B (display screen area 40) for example, the control user interface could be pre-programmed such that the user would be required to select a particular ultrasonic scan medical protocol for adjusting the TGC or time gain control for the ultrasound scan head. The help and comment area B could automatically remind the user that he or she must select the appropriate medical protocol for adjusting the TGC control on the ultrasonic scan head.

To carry this computer based and computer driven display system one step further, the virtual control user interface could block access to the subsidiary menus (for example, subsidiary menus in FIGS. 3, 4 and 5) until the user actually selects a medical protocol.

Further software blocks could added to the virtual control user interface which would require the user to input the name, age and sex of the patient and particularly identify the patient number or other relevant information before conducting an ultrasonic scan.

FIGS. 2, 3, 4A, 4B and 4C diagrammatically illustrate two embodiments of the subsidiary menu or secondary menu level below the time gain control TGC user interface.

Figure 2:
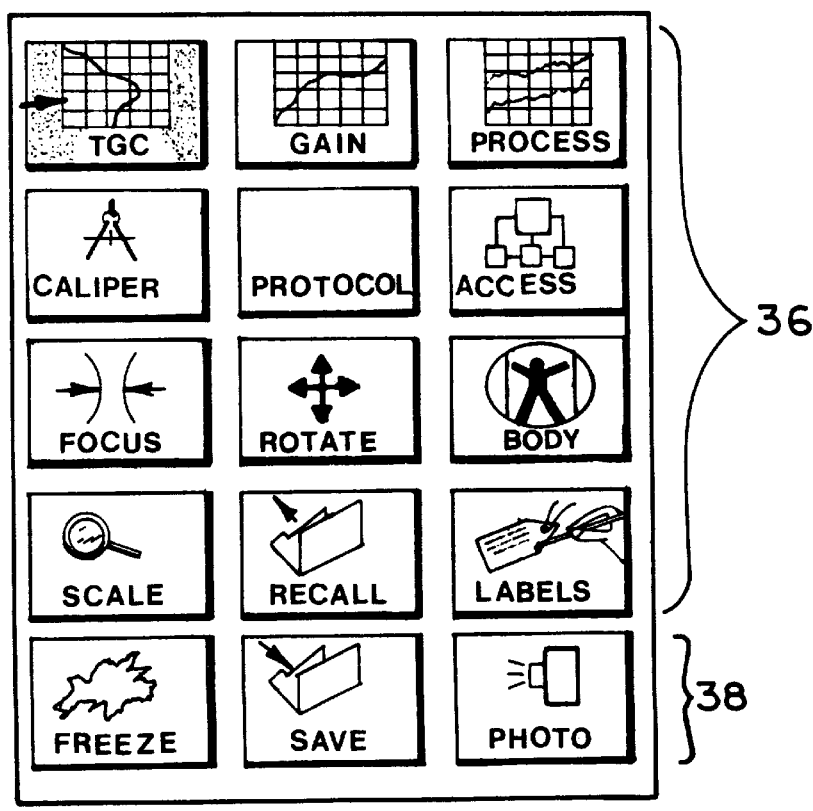
FIG. 2 diagrammatically illustrates another embodiment of the dynamic menu portion of the virtual control user interface.

FIG. 2 diagrammatically illustrates a dynamic menu region 36 and display screen area 38 which shows icon for the various commands or functions as well as the english language equivalent or abbreviations for those functions. In general, there are two different display embodiments discussed herein. These different embodiments are meant to reveal the flexibility of the virtual control user interface and not to limit the claims appended hereto. The icon shown in FIG. 2 show TGC as a vertically oriented curve since the TGC actually changes the sweep of the echo response generated by the ultrasound scan head, a gain icon which is a horizontally oriented curve, a process icon as two synchronized wave forms; a caliper or measurement icon revealed by an illustration of a caliper; protocol (which may be represented by a book or a note pad indicating which medical protocol should be selected for a particular ultrasonic scan), an access icon which reveals a central box with peripheral units connected from the central box (representing the ultrasound processor which is electronically connected to certain access items such as VCR's, CD ROM writers and readers, LANs modems and linked to enhanced computerized data bases), a focus icon, a rotate image icon comprising of four arrows outwardly directed from a central square; a body marker icon shown as a body; a scale or zoom icon illustrated by a magnifying glass; a recall image or electronic file icon shown as a file folder with an arrow pointing outbound therefrom, a label or annotation icon illustrated by hand holding a pen or a pencil which is writing on a note pad. In screen display area 38, icons representing a freeze image signal (shown as a snow flake), a save image icon shown as a file with an arrow pointed to the file and a photo icon shown as a camera.

The freeze function enables the user to take a freeze frame of the ultrasound image currently retained in the temporary memory of the ultrasound processor. As can be appreciated, the acquisition of ultrasonic signals occurs in real time and the ultrasound processor unit continuously receives new electronic signals from the ultrasound scan head. Once the operator identifies a particularly good image (represented by a multiplicity of electronic signals currently displayed on the display monitor), the operator can freeze frame that electronic image and further process that image as discussed hereinafter. The user functions of saving an electronic image as well as generating a photograph of the electronic image are fairly well known. Saving an electronic image enables the user to electronically store the ultrasound scan image into the ultrasound processor memory (discussed later in conjunction with FIG. 25) and further to save it into other electronically attached computer peripheral elements. The photo function is also readily apparent to users of preexisting ultrasound processors. For example with respect to obstetrical ultrasonic techniques, physicians may want a printed image of the frozen or selected electronic image captured by the ultrasound processor. The user can select the photo function and a polaroid type photograph is generated by the ultrasound processor or an appropriately configured peripheral equipment.

Figure 3A:
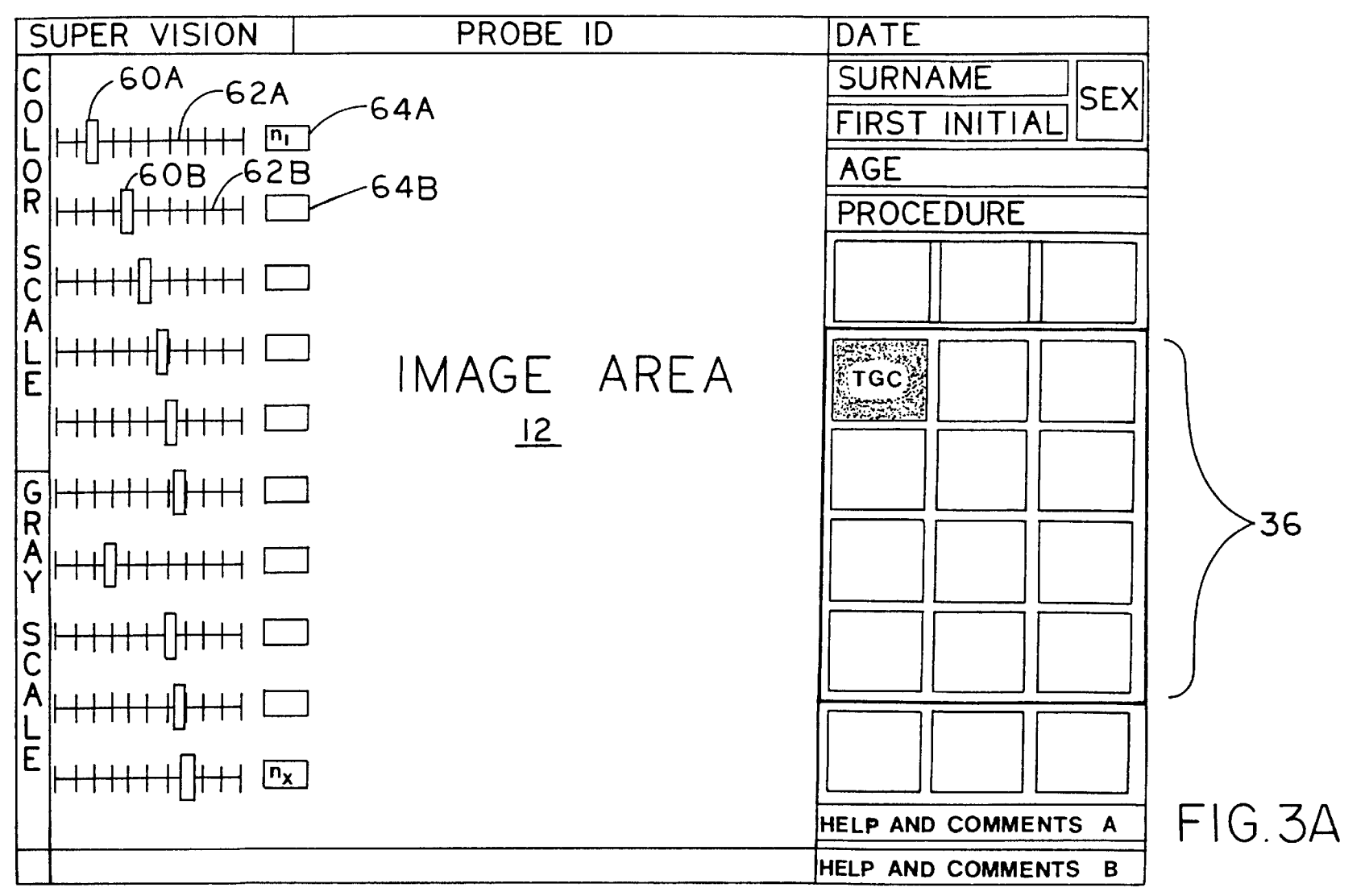

FIGS. 3A and 4A, 4B and 4C diagrammatically illustrate a secondary menu level associated with the TGC or time gain control virtual control user interface in accordance with the present invention. FIG. 3A, only the TGC functional element has been illustrated. Since the TGC or time gain control of the ultrasound processor affects generally the depths and echo responsiveness of the ultrasound scan head, users are generally accustomed to moving a plurality of slide switches or rotating a plurality of knobs to adjust the image and the depth of the image displayed in image area 12. In FIG. 3A, the virtual control user interface is configured with a plurality of user activatable slide or bar switches 60a, 60b, among others. To change the TGC at the upper level of scan image (for an illustration of the scan image, please refer to FIG. 14), the user would locate the cursor on the virtual image for slide bar 60a, click the mouse or actuate the push button on the track ball, drag the virtual image of the slide bar 68 to another point on virtual image track 62a and then release the mouse switch or track ball switch. Alternatively, a touch type display screen is utilized, the operator could simply touch the virtual image of slide bar 60a and move the slide bar along virtual image line 62a to the appropriate position. Simultaneous with this change, the sonographic image in image area 12 is changed. Accordingly, the virtual control user interface in the present invention not only changes the ultrasonic image captured by the processor but also acts as a control mechanism to control the response of the ultrasonic scan head. Immediately adjacent each virtual image slide bar control line 62a, 62b, is a display area showing the numerical value. Please refer to display 64a and 64b. To show the flexibility of the virtual control user interface, the user could save a particular screen setting or TGC screen setting using the save function. See menu bar area 38 in FIG. 2 or that same area in FIG. 1. Thereafter, the user could recall that TGC or gain setting for feature scans.

Figure 3B:
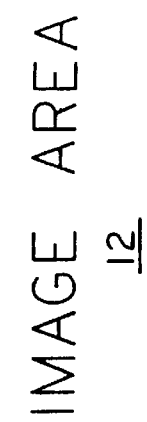
FIG. 3B diagrammatically illustrates the operation of the touch screen control sub-system.

FIG. 3B illustrates the concept that the touch screen is utilized to control the slide bar or TGC controls. Of course, the touch screen control sub-system described herein for the TGC controls can be used for other types of controls, i.e., the gain control. In this embodiment, the touch screen is divided into sectors or predetermined regions which overlap the ultrasonic image area. In FIG. 3B, these sectors are horizontal bars. When the operator touches a point on the active portion of the screen, for example point X1, the screen software routines generate a screen or a mouse event. The same commands are generated by the software if the mouse pointer is placed at position X1 and the mouse control is depressed. Similar responses are provided with a track ball. Upon generation of the screen event at position X1, the software locates that position with a digital positioning data. If the user moves his or her finger across the screen in band X (encompassing positions X1 and X2), the touch screen software generates a series of values which collectively represent the differential between positions X1 and X2. The virtual control program subject to the present invention then converts this differential into a slide movement of the TGC control bar from position dX0 to position dXn. Concurrently, the TGC control program generates a TGC command signal to the internal scan converter and the external video processor unit which alters the TGC control signals at that depth in the return sonic wave, i.e., the sonic echo. If the user moves from position X2 to position Y1, band Y activates and the system activates the TGC control associated with the Y band. Finger movement from position Y1 to Y2 changes the TGC control commands to the scan board and video processor unit as well as the displayed position of the slide bar in band Y. The slide bar moves from position dY0 to dYm. Position points Z1 and AA1 fall in bands Z and AA. The bands are not displayed to the user, they are invisible. However, the user can select any control simply by touching the screen. The Touch Control Table which follows is an example of this feature of the invention.

Touch Control Table

| Finger Position | Band | Screen | TGC-SCN Event | Knob |
| --- | --- | --- | --- | --- |
| x1 | x | activate | — | dxo |
| x2 | x | move x1 to x2 | dxo + (x2 − x1) | dxn |
| y1 | y | move x2 to y1 | — | dyo |
| y2 | y | move y1 to y2 | dyo + (y2 − y1) | dym |
| z1 | z | — | — | — |
| AA1 | AA | — | — | — |

Figure 4C:
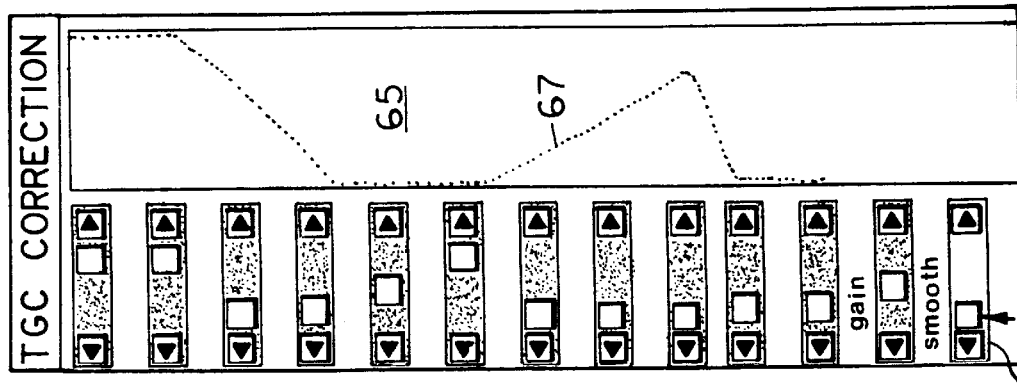
FIGS. 4A, 4B and 4C diagrammatically illustrate the TGC user interfaces in another embodiment.
Figure 4B:
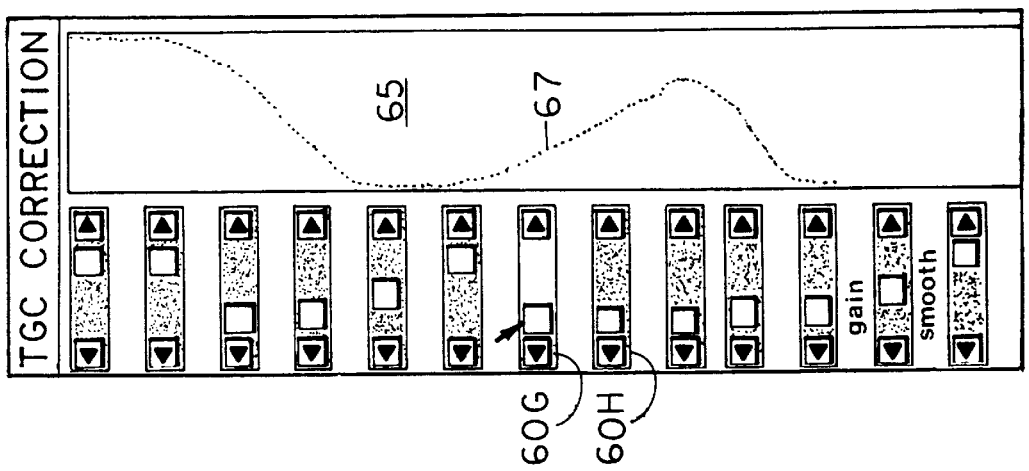
Figure 4A:
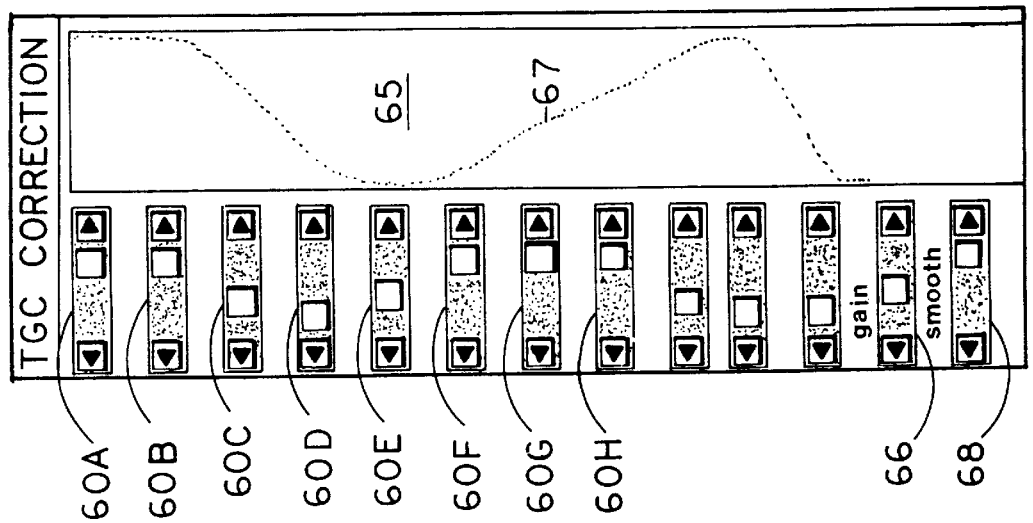

The flexibility of the present invention is also illustrated by reviewing the sequential figures of FIG. 4A, 4B and 4C. In these figures, slide bar switches 60a and 60b are illustrated immediately adjacent the line representation of the signal generated by the ultrasound scan head. This is shown in graphic region 65. FIG. 4B illustrates that the cursor has been placed proximate virtual image of slide switch 60g and that slide switch has been changed to reduce the gain at that particular vertical location. Slide switched 60g and 60h have been changed and the height of curve 67 has been changed is noted by a comparison between FIGS. 4A and 4B.

The control user interface is shown in FIGS. 4A, 4B and 4C also include gain control slide switches 66 as well as smoothing function slide images 68. In comparing FIG. 4A and FIG. 4C, the smooth switch 68 has been changed and curve 67 is shown as distinctly linear as compared with the curves shown in FIGS. 4A and 4B. Of course, the actual virtual control user interface can be altered to include a larger number or a smaller number of slide switches then illustrated in FIG. 4 or FIG. 3A. Also, when the sophistication of the ultrasound scan head improve, the user can simply replace the scan head interface unit (discussed in conjunction with FIG. 25), update the virtual control user interface software (illustrated in conjunction with FIGS. 1–24) without having to completely discard the ultrasound processor. Further, improvements in the control user interface can be easily adopted through the use of the software driven display modules illustrated herein. The software driven display module can be easily changed as compared with the hardwired or hardware control configurations for other ultrasound processors.

Figure 5:
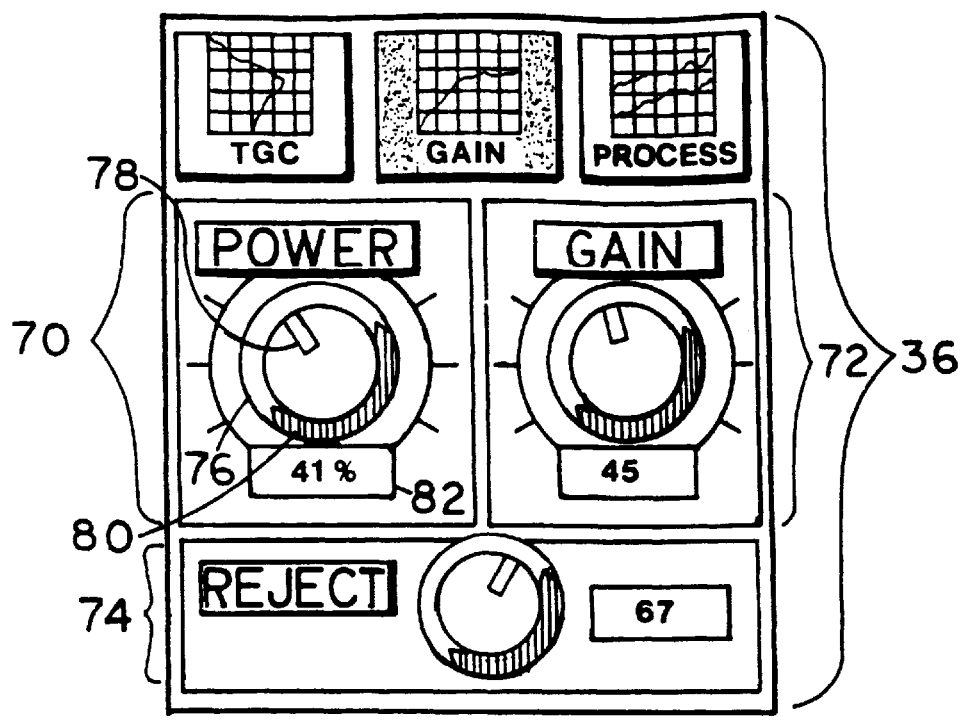
FIG. 5 diagrammatically illustrates the dynamic menu portion and sub-menu for the gain control interface.
Figure 6:
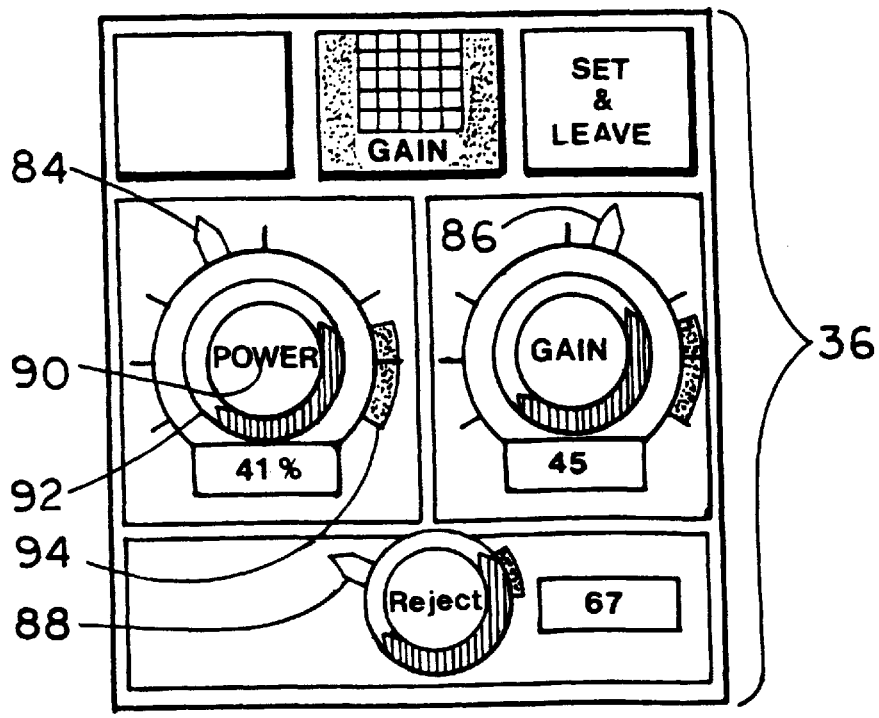
FIG. 6 diagrammatically illustrates another embodiment of the gain control secondary menu.

FIGS. 5 and 6 diagrammatically illustrate the secondary level associated with the gain function. FIG. 5 illustrates the use of virtual images of control knobs which the user may be accustomed to for a given hardware control configuration for another type of ultrasound processor. FIG. 5 illustrates that the user has activated the gain function from the main menu (see FIG. 1 and 2) and the dynamic menu window 36 now reveals virtual images for the control knobs controlling the power (area 70) and the gain, area 72, and the reject signal control area 74. With respect to virtual image power area 70, a knob 76 is illustrated. Knob 76 has a virtual image line indicator 78 as well as red color danger areas 80. The red color danger areas are in a partial arcuate ring beginning at approximately 60% of total power level. The power level virtual display also includes a numerical display 82 which reveals to the operator of the actual power percentage level generated by the ultrasound scan head. The gain menu area 72 and the reject menu area 74 are similarly configured with virtual images of control knobs as well as those knobs indicating overload or danger areas indicated in red or other distinctive display colors in an arcuate band about the central rotative position.

If a touch type screen is utilize, the operator would touch the radial end of lineal position marker 78 (see power menu area 70) and move his or her finger in a clock wise or counter wise manner about a pivot point generally in the center of the virtual control panel.

FIG. 6 diagrammatically illustrates another virtual control panel for the gain wherein the virtual knob controls include protruding virtual tabs 84, 86 and 88. If a touch type display screen is utilized, the operator would simply touch virtual knob 84, 86 and 88 and rotate his or her finger clock wise and counter wise about a central pivot position one of which is pivot position 90 for power knob 92. Also. FIG. 6 diagrammatically illustrates danger zones as shaded areas around the virtual knobs. One of these danger zones is shown as danger zone 94 around virtual knob 92, the virtual power control. FIG. 6 also illustrates a further functional aspect a "set and leave" command area that may be selected by the user.

Once selected, the user can exit the sub-menu for the gain control. Another way the user can exit a particular sub-menu is to simply move the cursor beyond the dynamic window and actuate the control button on the mouse or the track ball.

Figure 8:
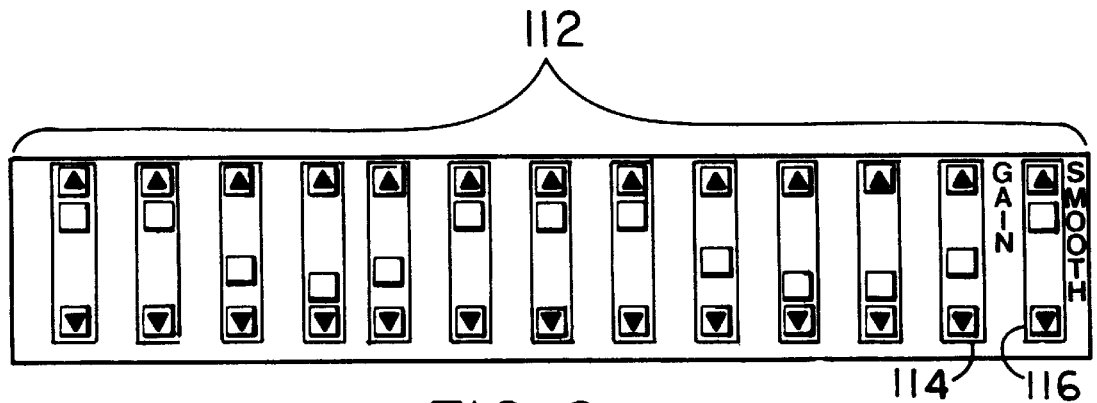
FIG. 8 diagrammatically illustrates a second embodiment for the image enhancement control user interface.
Figure 7:
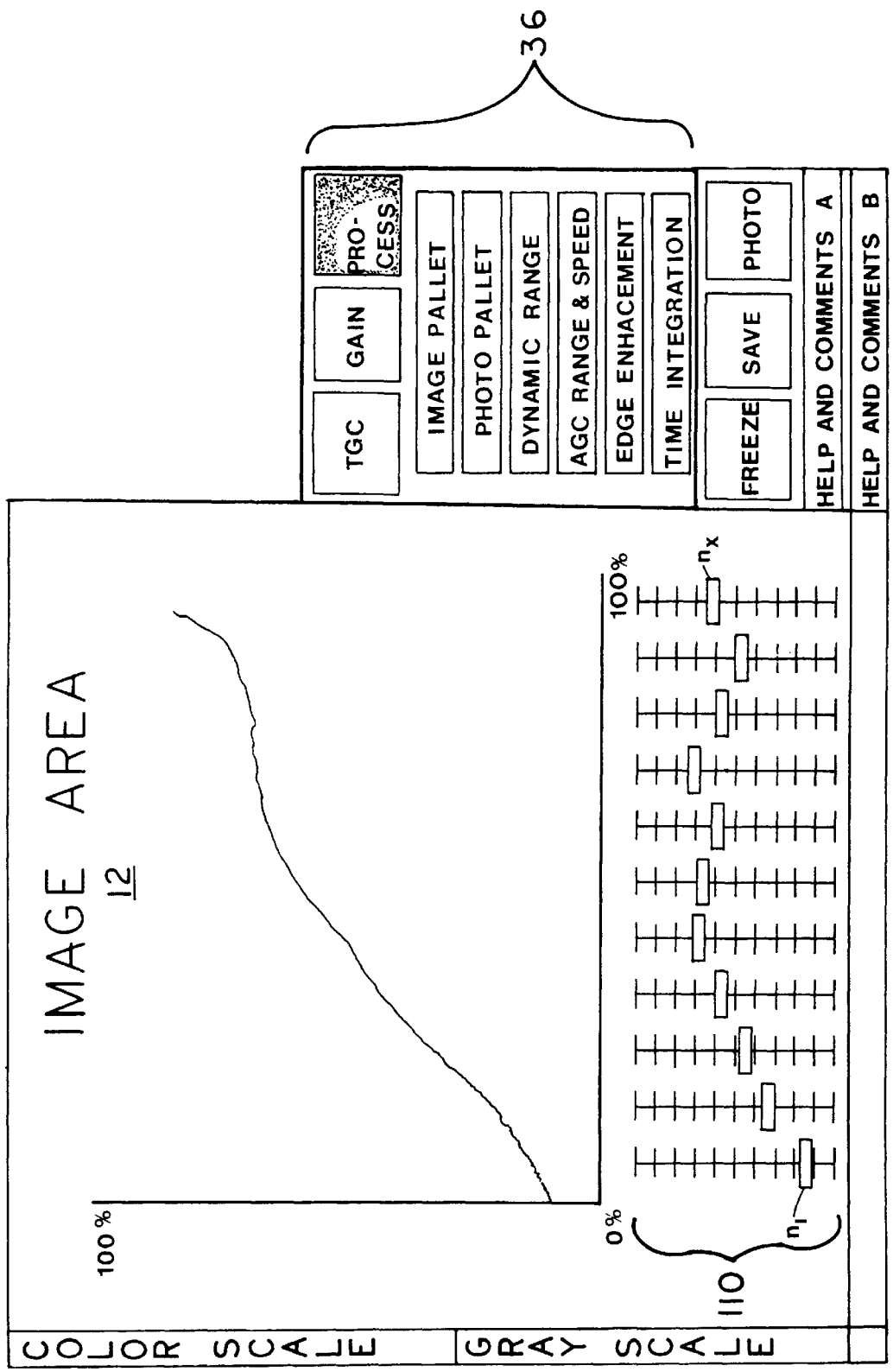
FIG. 7 diagrammatically illustrates a portion of the virtual control user interface sub-menu for the process or ultrasound image enhancement control interface.
Figure 9:
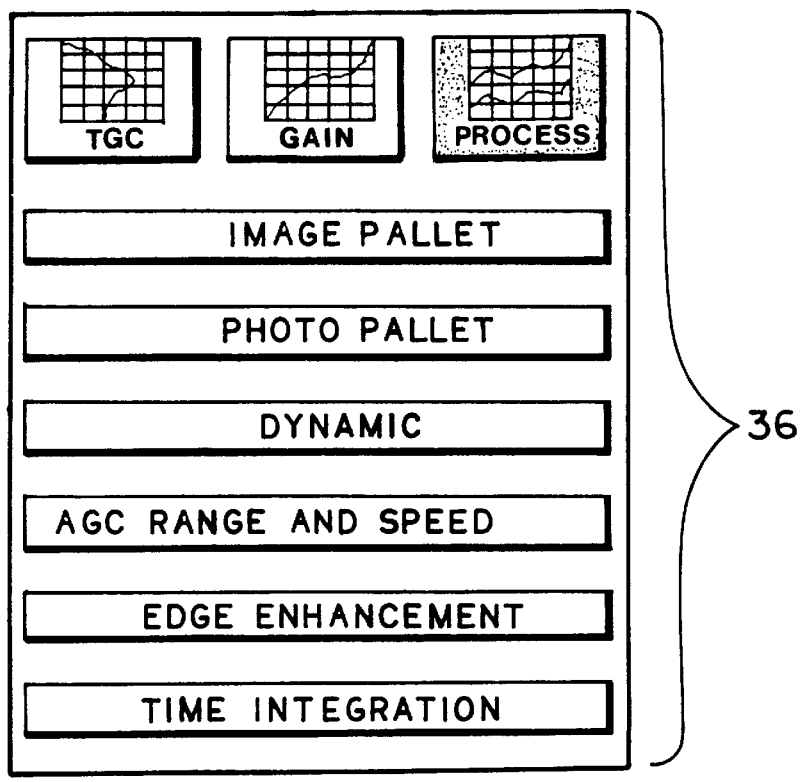
FIG. 9 diagrammatically illustrates a second embodiment of the dynamic menu window for the process sub-menu.

FIGS. 7, 8 and 9 illustrate various embodiments for the process sub-menus.

One embodiment is shown in FIG. 7 wherein the dynamic display window 36 illuminates the process functions and shows various options available to the user to control the processing of the ultrasonic electronic signals obtained from the scanhead. This processing includes changing the pallet on the image displayed in image area 12, changing the photographic pallet or color mix, changing the dynamic range for the scan signals, changing the automatic gain control (AGC) range and the speed or timing function for AGC enhancing the edge detection of the scan signal and providing time integration for the scan signal. As noted earlier, when the user moves the cursor over one of these areas, for example, image pallet as compared with dynamic range, that particular menu selection is highlighted or lights up. If the user wishes to activate that particular function, the user clicks the mouse button or tracking ball button or, in a touch screen situation, touches the screen to actuate the third menu level.

In the process menu, the image area is some what reduced and a pop up virtual control interface is displayed in lower region 110. As shown in FIG. 7, this virtual control interface consists of a number of slide switches $n_1$ through $n_x$ which can be actuated or moved by the user simply by placing the cursor on one of the virtual images of the slide bar and dragging the slide bar to the appropriate lineal position as indicated by the lines associated with each slide bar. As a further development, the actual power level or number could appear in the interior of the slide bar box. For example, $n_1$ could display 10% as being the image level for that particular range.

FIG. 8 diagrammatically illustrates another configuration for the process controls using a plurality of slide switches 112 two of which are shown as slide switches 114 and 116 which control the timing gain of all the signals as well as the smoothness characteristic of the video scan processor. This virtual control feature is diagrammatically illustrated above in conjunction with FIGS. 4A-4C.

FIG. 9 diagrammatically illustrates dynamic menu window 36 showing the process sub-menu activated and indicates sub-level user control commands to effect image pallet, photo pallet, dynamic range, AGC range and speed, edge enhancement and time integration.

Figure 10:
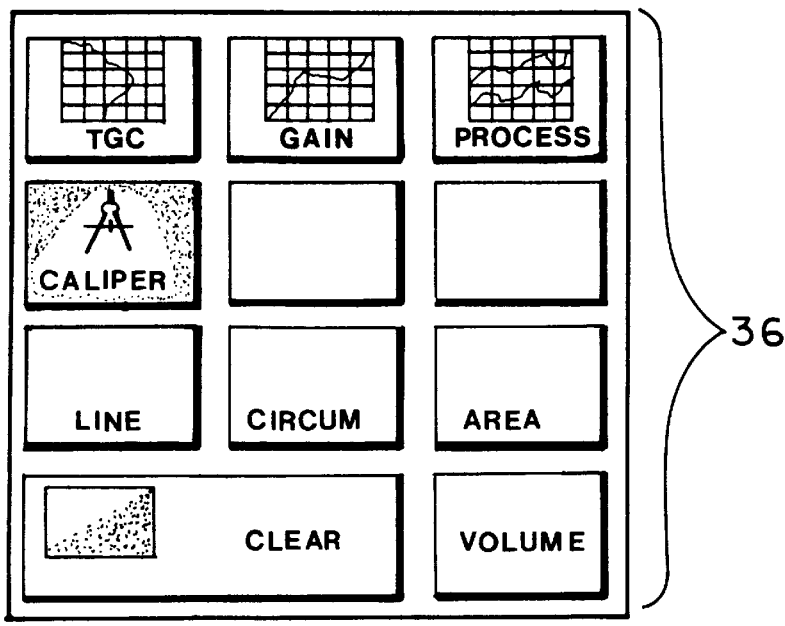
FIG. 10 diagrammatically illustrates one embodiment of the sub-menu display for the caliper or measurement user interface.
Figure 11:
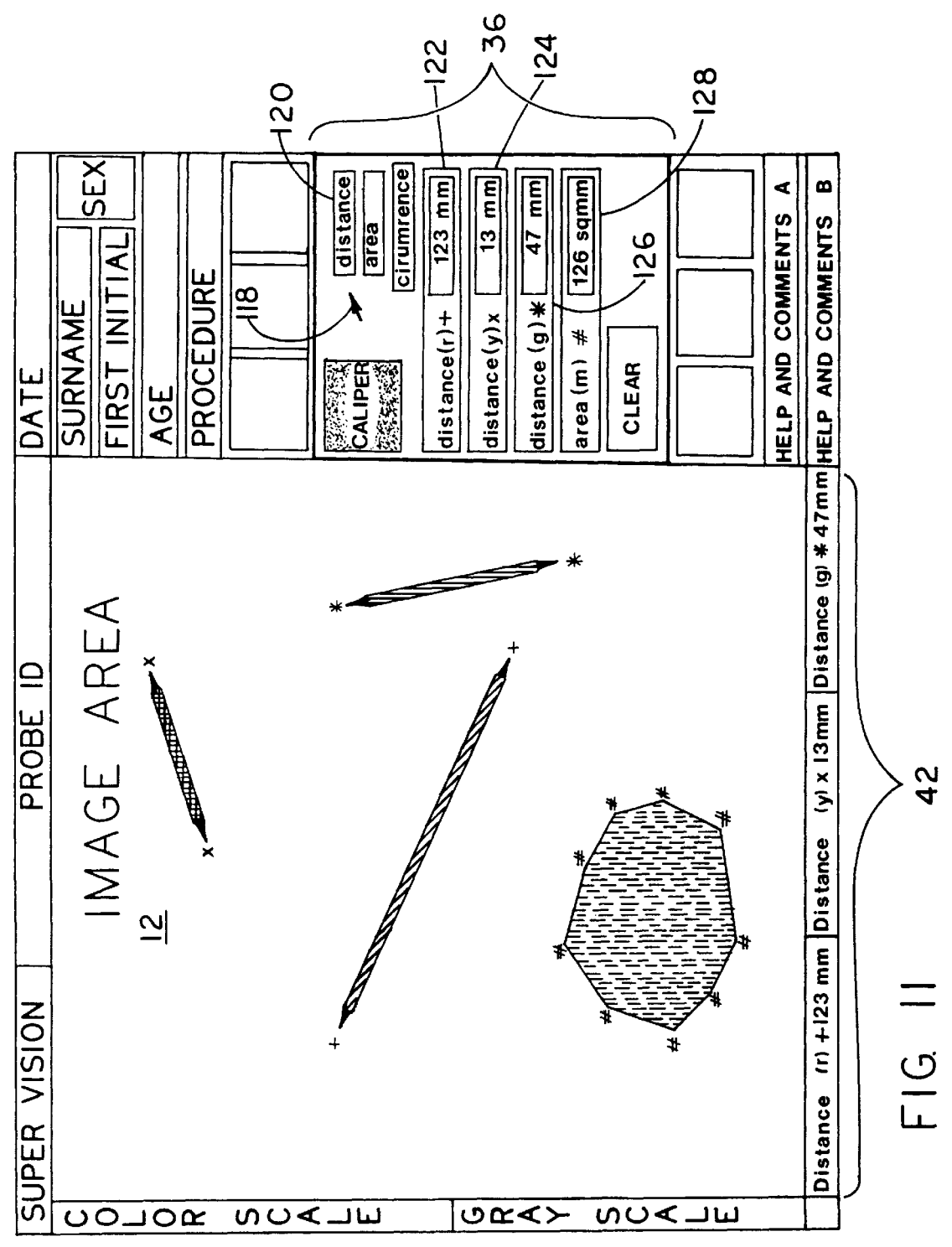

FIGS. 10 and 11 diagrammatically illustrate the caliper sub-menus which relate to measurement functions available to the user via the virtual control user interface. FIG. 10 shows that dynamic menu window 36 includes an illuminated caliper button as well as reveals function buttons for measuring lines, measuring circumference, measuring area and measuring volume. Further, a function button enabling the user to clear a particular line is found in dynamic window menu 36. FIG. 11 shows a slightly different configuration with a cursor 118 proximately adjacent distance function button 120. Dynamic window 36 displays distance figures in region 122 (shown in red between the small plus signs in image area 12, the yellow distance shown between X's in image area 12, and a green distance G shown by asterisks in image area 12). The green line is illustrated on the image in a green color and is shown in green in display region 126. In the screen area 128, an image area is illustrated in magenta (M) and is highlighted in that color in image area 12. In the lower menu region 42, the red distance, yellow distance and green line distance is shown in order to assist the user.

The ability of the user to mark and measure the distance on a sonographic electronic image is important. For example, when using an ultrasound technique in conjunction with fetal development, the obstetrician seeks information regarding the length of certain fetal limbs as apparent in the ultrasonic electronic image. By enabling the user to easily control the processing of this ultrasound image (through TGC and gain virtual controls) and enabling the user to freeze that ultrasonic image on the screen (see for example FIG. 2, menu region 38 and the freeze control therein), the user can easily mark the image and actually make electronic drawings and immediate measurements for the physician and other health professionals interested in this information. The use of different colored lines and different display significantly enhances the operability and the user friendliness the present system.

Figure 13:
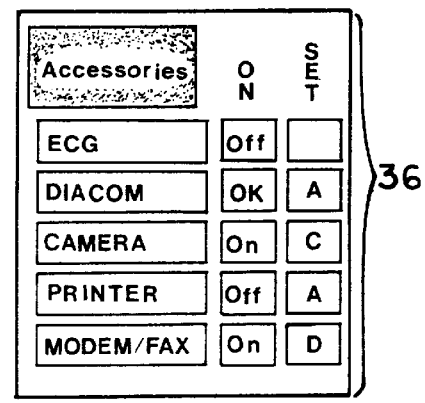
FIGS. 12 and 13 diagrammatically represent two embodiments for the dynamic window display for the accessories or access sub-menu level.
Figure 12:
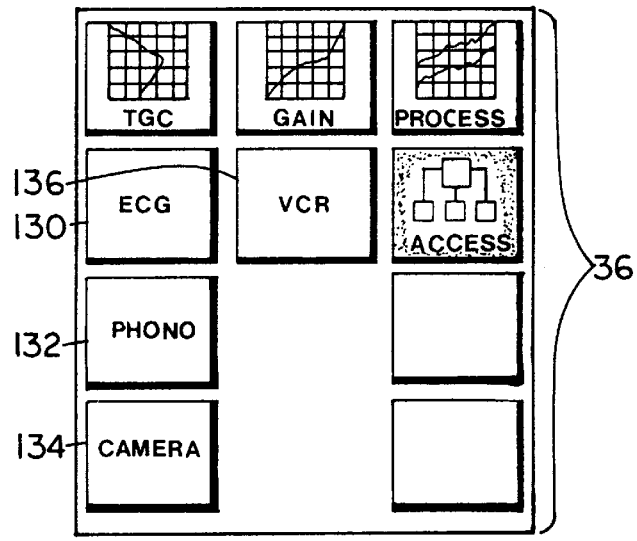

FIGS. 12 and 13 diagrammatically illustrate the access or accessory sub- menu for two embodiments. FIG. 12 shows menu buttons for electrocardiograph information (ECG) virtual menu button 130, phonographic or audio acquisition and access to other peripheral equipment on menu button 132, access to a camera peripheral equipment on virtual button 134 as well as access to a video tape recorder or VCR on menu button 136.

With respect to FIG. 13, other accessories are available such as a printer or a modem/facsimile machine. The preferred virtual control user interface incorporates a toggle on or toggle off type switch. However, as shown in FIG. 13, it may be appropriate to list the availability and on line accessibility of this equipment through various electronic computer ports.

With respect to FIG. 12, the photographic or audio linkage could be in the case of obstetrical use, the linkage of sounds obtained from a fetal monitor as well as the sonographic electronic file information. If this information from the audible fetal monitor as well as the electronic image from the sonogram taken of the pregnant mother is transferred to a specialist, the specialist at a very remote location could assess the condition of the mother by reviewing this information at his or her leisure. The ability to electronically obtain these signals, log these signals in and out of the system and store them in an electronic file as well as transfer this electronic file to others is an important feature of the present invention.

Figure 15:
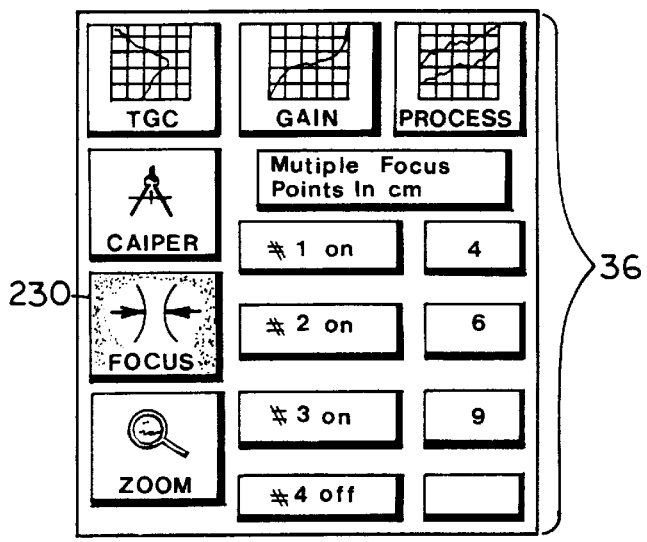
FIG. 15 diagrammatically illustrates the dynamic menu window for the focus control sub-menu utilized in conjunction with a second embodiment of the present invention.
Figure 14:
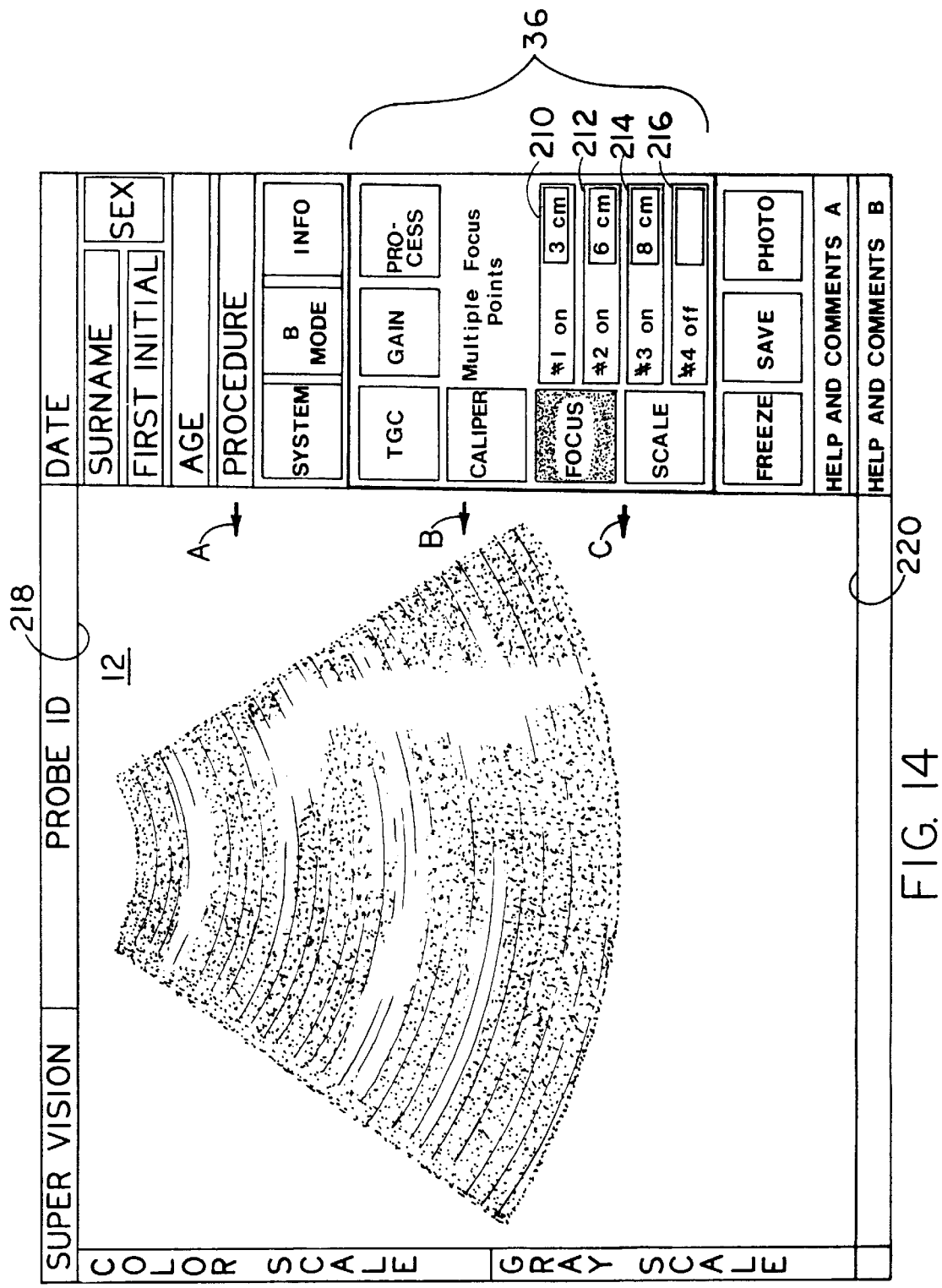
FIG. 14 diagrammatically illustrates the virtual control user interface for the focus control sub-menu and particularly one scanned image displayed in conjunction with the user interface.

FIGS. 14 and 15 diagrammatically illustrate the sub-menu levels for the focus control virtual function. In FIG. 14, an ultrasonic scan signal is illustrated. The focus virtual control button has been illuminated. Display areas 210, 212, 214 and 216 reveal the multiple focus points available to the operator. Particularly, focus points 1, 2 and 3 are on and the tissue depth is illustrated for each focal point. Focal point 4 is off. Arrows a, b and c correspond to focal points 1, 2 and 3 and as displayed as such, the operator can change, for example, focal point 3, arrow c, by moving the cursor to arrow c and dragging arrow c to a point all the way to the top of the screen or at level 218 or all the way to the bottom of the screen at level 220. It should be noted that the illustrated ultrasound image is only exemplary in nature and may actually fills the entire image area 12. Also, it should be noted that the operator can drag any of the focal points beyond the other focal points already fixed.

FIG. 15 illustrates and alternative embodiment for the dynamic display window region 36. Focus button 230 has been illuminated and the operator has turned on focal points 1, 2 and 3 but focal point 4 is off.

Figure 16:
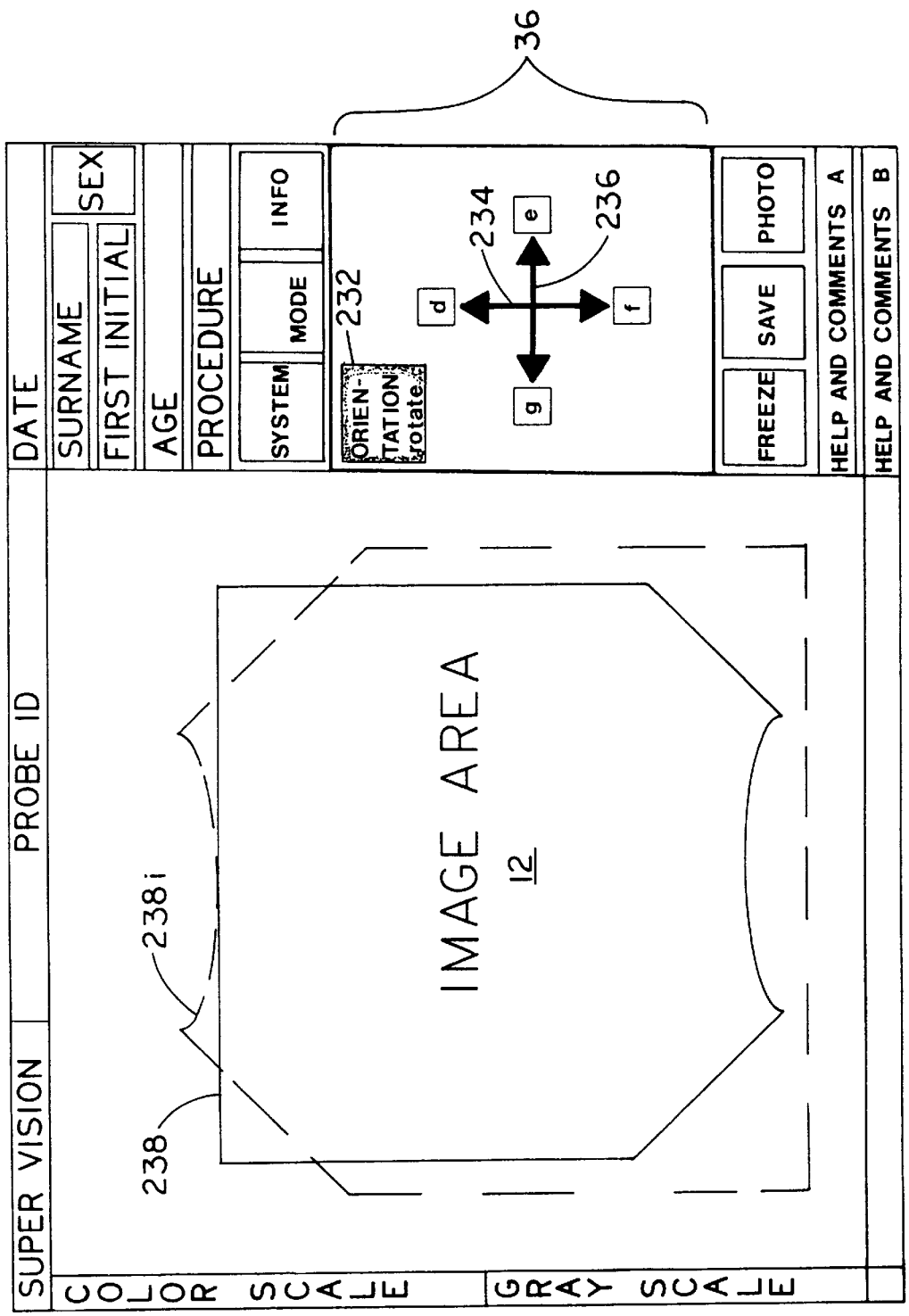
FIG. 16 diagrammatically illustrates the sub-menu level for the orientation or rotate image menu.

FIG. 16 diagrammatically illustrates the rotate image or orientation menu level such that rotate menu button 232 is illuminated. One virtual control interface could include the use of horizontal and vertical lines 234 and 236 each having an arrow head at opposing ends. Function buttons d, e, f and g may be placed at the terminal ends of those arrow heads. In a touch screen user interface, the user can simply touch display button d and move it up or down thereby moving the image 238 up or down or otherwise rotating the image clock wise or counter clock wise by simply rotating button d in the appropriate manner. Image 238 is rotated 180° as shown by image 238I in dashed lines in FIG. 16.

FIGS. 17, 18 and 19 diagrammatically illustrate the body marker or scan position virtual control user interface for the present invention. In FIG. 17, the body marker menu button 250 is illuminated and the operator can select from this sub-menu an image view 252, an icon placement function 254 and a probe placement function 256. As shown in FIG. 17, a rectilinear image block 260 has been placed on the left hip region of the female image. This indicates that the user has scanned that general region of the patient. FIG. 18 diagrammatically illustrates front and back views of a male as user markable icons 272 and 274. FIG. 19 is a further menu selection enabling the user to select a particular scan icon such as by selecting rectilinear bar icon 276, Y bar icon 278 or arrow head icon 280. Function command 282 enables the user to rotate the particular scan icon along the body icon 290 or 292. In this illustrated embodiment, the body icons are provided with a plurality scan positions generally illustrated as a plurality of arrow heads 294 directed to the right side of the front of the female body. Of course, the virtual control user interface may have a plurality of arrow heads pointing and surrounding the body icons. In this embodiment, the user would select the appropriate position icon by positioning the mouse or track ball curser on the particular body position icon and selecting the position elements by depression of the mouse or track ball key. Also the user can select the type of scan icon used at that body location. The program would then locate the selected scan icon at the selected body location. The user would also be able to rotate that scan icon to the appropriate position. This is shown with respect to body icon 292 wherein rectilinear scan icon 296 has been positioned at the lower back of body icon 292. The scan number has been displayed in display region 298. In the lower region 299, the operator is reminded of the current scan number which should be identified in conjunction with the ultrasonic scan acquired by the operator.

The body marker and various secondary and third menu sub-levels may be particularly helpful when used in conjunction with protocol function. In other words, the user may select a particular protocol from the protocol function menus and then call up the body marker in order to assist the user to properly scan the correct area on the patient. Simultaneous with this scanning and acquisition and signal processing by the user, the virtual control user interface could prompt the user to scan certain positions on the patient. This prompting could be incorporated as part of the body marker menu function.

The following protocol table illustrates the potential of the protocol menu function button (see FIG. 2). In the Protocol Menu Table which follows, the basic protocol for determining a certain kidney condition includes pelvocaliceal scans in multiple positions.

Protocol Menu Table

A. Basic Protocol
 Outline Kidney
 Pelvocaliceal Scan Echo
 Position 1
 (move 5 cm)
 Position 2
 (move 5 cm)
 Position 3
B. Supplemental (Baker) Protocol
C. Dr. Kelly's Protocol The protocol menu function could be coupled with the body markers in order to require the user to scan a minimum of three positions in order to fulfill the basic protocol. Upon storing and filing the three scans (using the save menu function button (FIG. 2)), the user would check off each element in the basic protocol. As stated in the protocol menu table, the user would be required to outline the kidney, and scan the enteral body organ in three positions as specifically stated in the protocol.

If the physician ordering the sonogram wanted to use a different or a higher level protocol, the physician or other medical technician could load in this other protocol (the Baker protocol) and the Baker protocol could be listed for the user. Further, in some instances different doctors in the same medical office may want scans at different levels or at different frequencies. The protocol menu function button could provide this.

Figure 20:
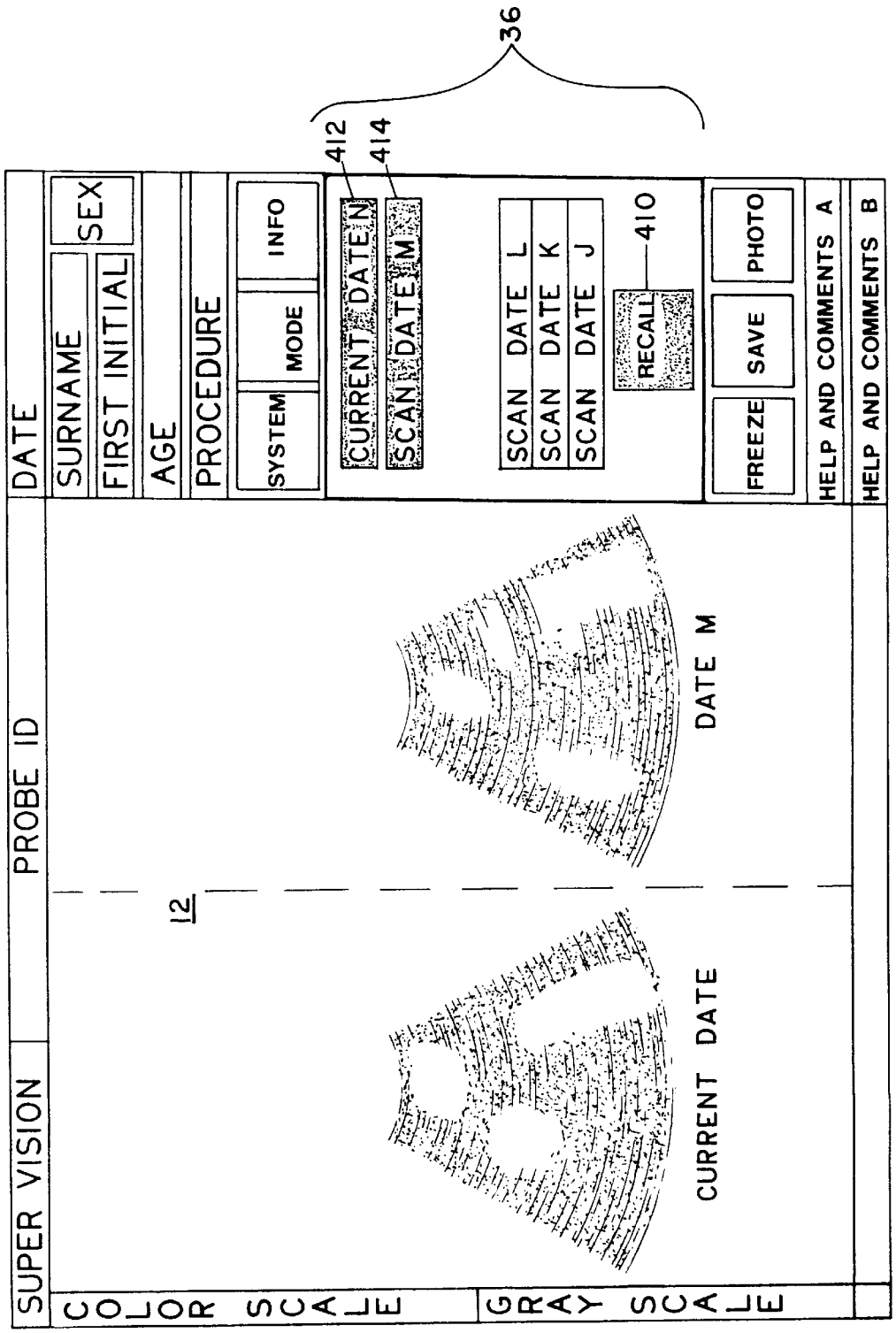
FIG. 20 diagrammatically illustrates the virtual control user interface showing a pair of ultrasound scanned images, one from an earlier scan and one from the current scan wherein these dual scan images are part of the recall sub-menu.

FIG. 20 diagrammatically illustrates the recall virtual control user interface. In the recall function, menu button 410 is illuminated and image display area 12 is divided into two sections, the first section showing a current scan (identified with the current date) and an earlier scan image identified by showing scan date M. In the illustrated instance, the user has selected menu button 412 showing the current date N and the earlier scan image of scan date M at function 414. The user has the ability to call up other scans, particularly those acquired at date L, date K and date J. With this feature, the user could configure electronic files showing the progression or regression of a certain disease.

Figure 21:
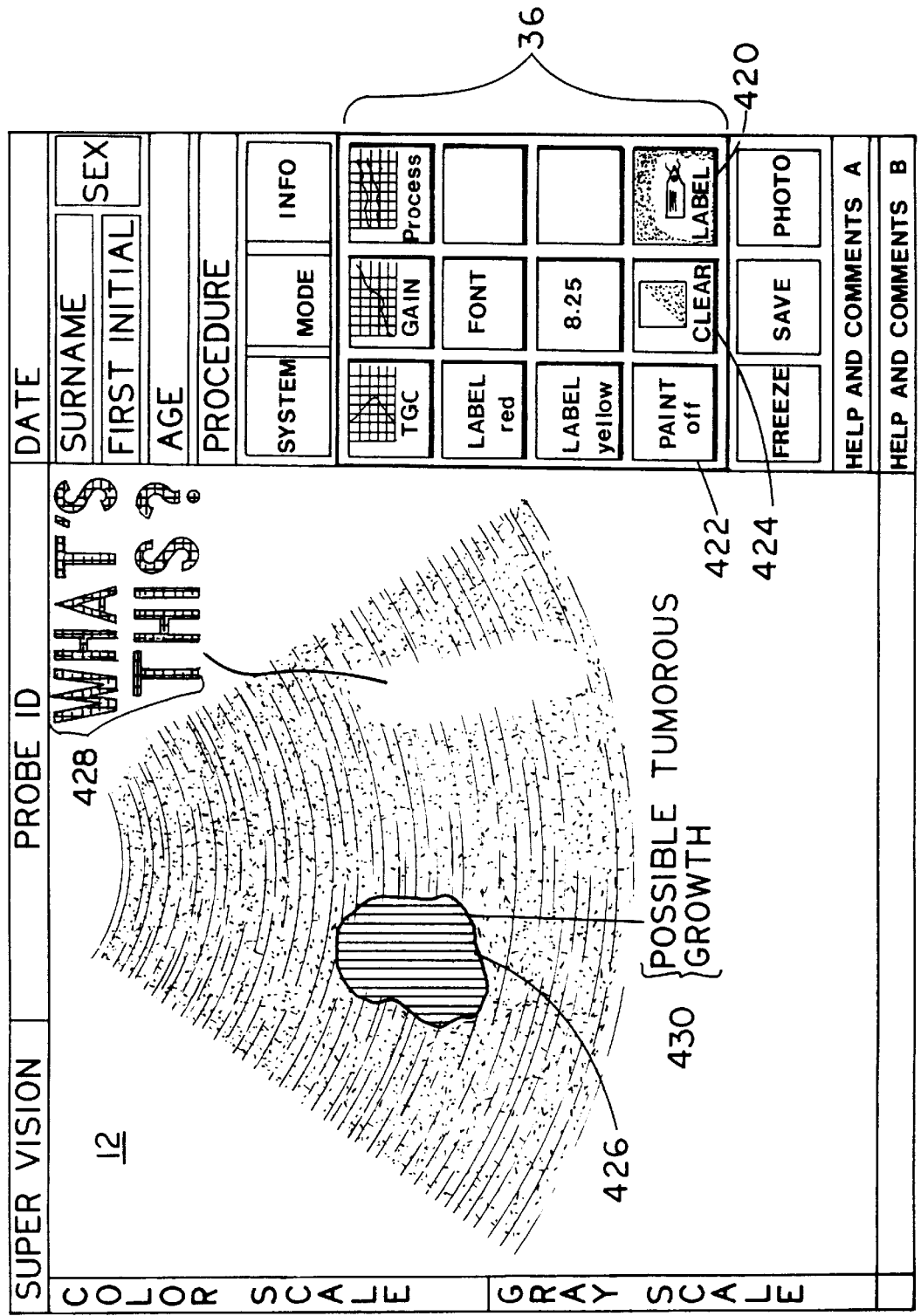
FIG. 21 diagrammatically illustrates the annotation feature of the control user interface.

FIG. 21 diagrammatically illustrates the sub-menu level for the annotate or label menu function. In this instance, the label or annotate menu button 420 is illuminated and dynamic menu display area 36 shows functional buttons for applying red labels, yellow labels, selecting the size of the print (which is commonly known as font size), as well as a paint ON or paint OFF function button 422 and a clear function button 424. In the display image area 12, the physician has circled a region 426 in, for example, a red color and has typed the term "possible tumors growth" in order to highlight this region for other health care professionals. In contrast to this red annotation on the electronic scan image is a yellow annotation "what's this" and a line leading to a certain electronic image region on the ultrasound scan. This different color annotation is identified in FIG. 21 with a double line. Also, the font size has been increased in text region 428 as compared with text region 430.

The annotations may be electronically stored in a separate file or maybe electronically stored in conjunction with the scanned image. If stored with the scan image, it may be necessary to enable the user to remove the annotations prior to viewing. For example, with respect to the recall function shown in FIG. 20, it may be preferable to remove the annotations from the recall image scan and to view the image scan side by side without any annotations. Also, it might be important to include in FIG. 20 the ability to recall in the annotations in the previous scan with a toggle on or toggle off menu button.

Figure 22:
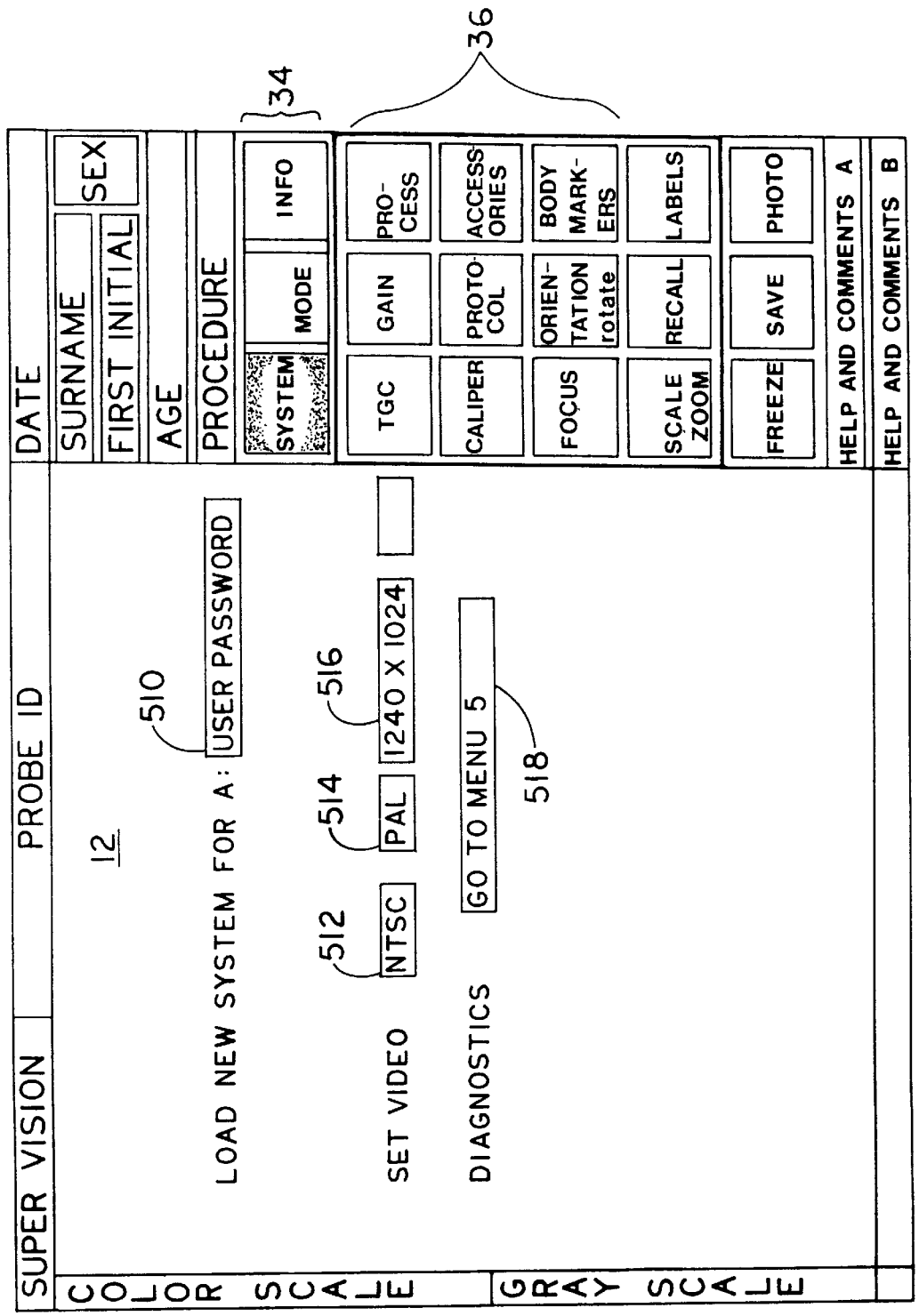
Figure 23:
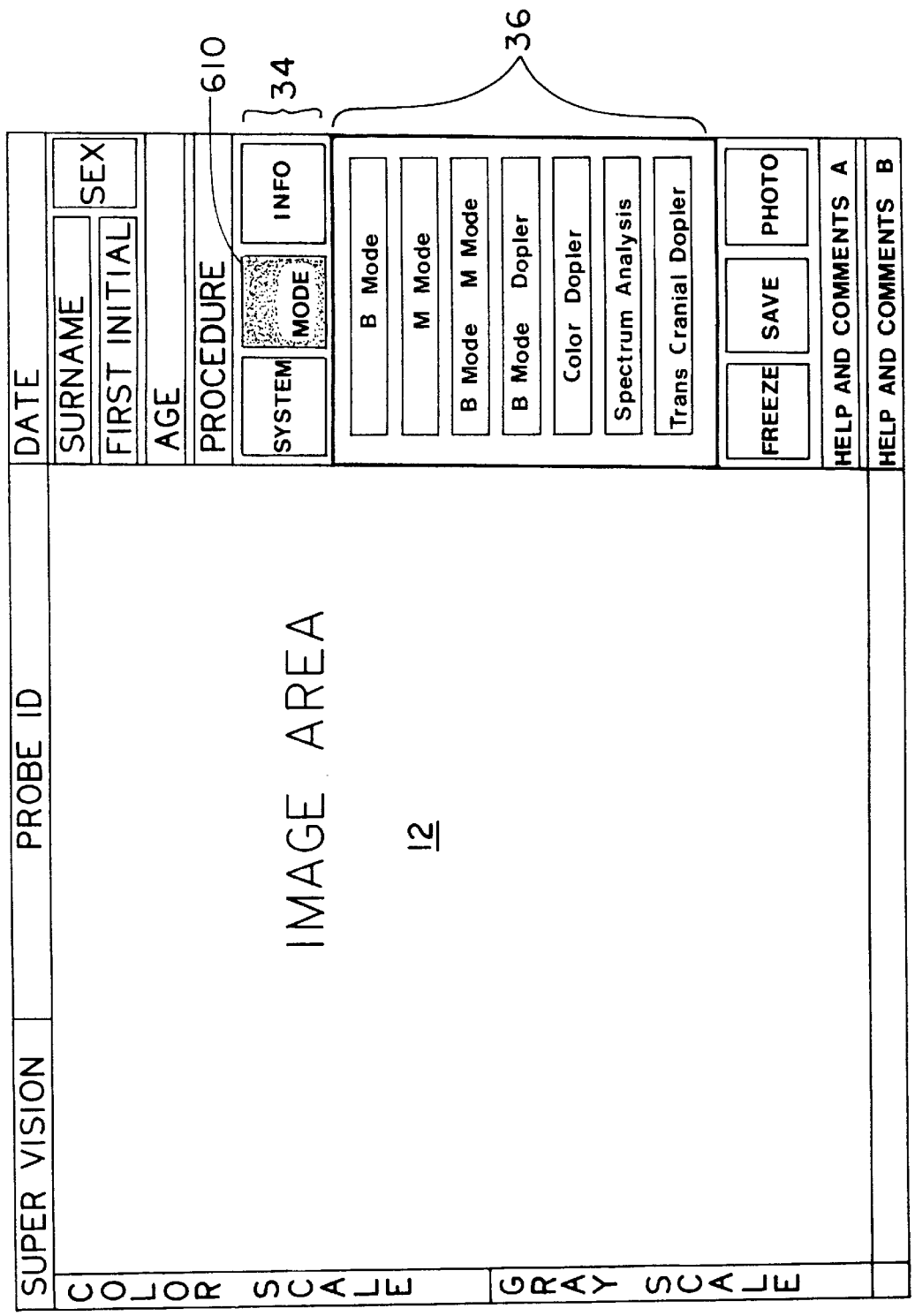

FIGS. 22, 23 and 24 diagrammatically illustrate certain overall features systems associated with menu bar 34 from the main menu. In FIG. 22 the system menu has been illuminated and the user is required to input his or her password or user Id in space 510, is required to set the video connection to NTC or PAL in section 512 and 514 and also to establish the size of the screen in display box 516. In order to enhance the user interface, the virtual control user interface may provide menu selections for the operator to select one of a plurality of selections to set up the system conditions. Menu box 518 enables the user to diagnosis and test the ultrasound processor as well as the ultrasound scan head and scan head interface unit.

In FIG. 23, the mode function button 610 has been actuated and therefor illuminated. In dynamic menu area 36, the operator can select which mode the ultrasound scan head is operating in, that is, b-mode, n-mode, b mode and m mode b mode and doppler, color doppler, spectrum analysis (involving a frequency analysis of the scan signal) or transcranial doppler mode. Of course, the virtual control user interface can be modified in the event other ultrasound scan heads and general processing routines become available to the user. - In FIG. 24, the information or info menu button has been selected from menu bar 34. Further, menu bar 34 indicates that mail has been received by the ultrasound processor in spot 710. The information displayed in image area 12 provides general instructions for the user, for the renal transplant scan. This is somewhat similar to the protocol but really provides a mail box type environment where the user is instructed to use a certain type of ultrasound scan head and request certain scans such as length, width and depth as well as to send certain electronic files to physicians for their further input. Dynamic menu area 36 shows other available routine such as patient information, procedure information (currently displayed in image display area 12) protocol information, appointments, measurements leave a message (for electronic mail) and supervision notes.

Returning to the main display menu in FIG. 1 and particularly the zoom or scale function button, the user, upon actuation of that function, can select the degree of magnification or complete enhancement of the scan image appearing in image area 12.

FIG. 25 diagrammatically illustrates the hardware for the ultrasound processor 810. In one embodiment, ultrasound processor 810 includes an enteral bus 820 connecting a peripheral input/output card 822 with a modem card 824, a small computer system interface (SCSI) 826, a mother board 828, an ultrasound 29 scan head interface card or unit 830 and a local area network input/output card 832. Mother board 828 includes random access memory or RAM 834 as well as a CPU or central processing unit chip 836. The CPU chip controls the handling of information and instructions on enteral bus 820 the ultrasound scan head interface unit 830 is connected to an ultrasound scan head 840 as well as to a photograph production unit 842. The SCSI board 826 is connected to a CD read and write player 844. Modem 824 is connected via the telephone company 846 to a data base computer file 848. Computer peripheral input/output board 822 is connected to a local printer 850, a display monitor 852 (which may be a touch screen monitor) to a mouse 854 as well as to a keyboard 856. Keyboard 856 may additionally have a track ball 858 thereon.

The local area network input/output board 832 is connected to a file server 860 which in turn is connected to computer system $D_{r1}$ computer system $D_{r2}$ as well as telephone company 862 and a further computer system $D_{r3}$ file server 860 is also connected to remote printer 864.

An important aspect of the present invention is the ability to interconnect the ultrasound processor electronically to other computer data base files (data base files 848 via telephone company 846 and modem 824) as well as CD read-write units 844 in order to provide the user with the ability to quickly update any protocol and share the medical information provided by the accumulation of scanned data.

In the event the physician or the medical office wishes to up grade its ultrasound processor, the processor is simply disassembled and one of the cards is removed while another card is replaced. For example, the physicians may want to upgrade CPU 836 from a 486 machine to a PENTIUM or 586 type machine. This can be accomplished simply by removing mother board 828 and installing a faster mother board. Mother board 828 is further connected to a floppy drive 870, a hard drive 872, and a magnetic tape 874.

Further, since the electronic images can be annotated and protocol established and made uniform throughout the entire medical office, the physician or other medical technician may share this electronic file with other physicians at computer systems $D_{r1}$ and $D_{r2}$ and even medical offices at very remote locations such as $D_{r3}$. In addition, the billing procedure for recapturing the cost for the ultrasound scans are easily enhanced. For example, the file server 860 can periodically poll ultrasound processor 810 in order to obtain information regarding the number of scans and the type of scans obtained on that processor. Further, with the integration of the present ultrasound processor system in the surgical arena, the current and earlier ultrasound electronic images could be delivered directly to the operating room such that the physician or surgeon conducting an operation can visually perceive the progression or regression of a particular disease or abnormality in a patient during the operation. Further, the surgeon can see critical areas like blood vessels, urethrae, etc.

In one embodiment, the present virtual control user interface utilizes a 486 INTEL processor with approximately 1–2 mega bytes of RAM. Now, the system uses 4–8 bytes of RAM.

Figure 26:
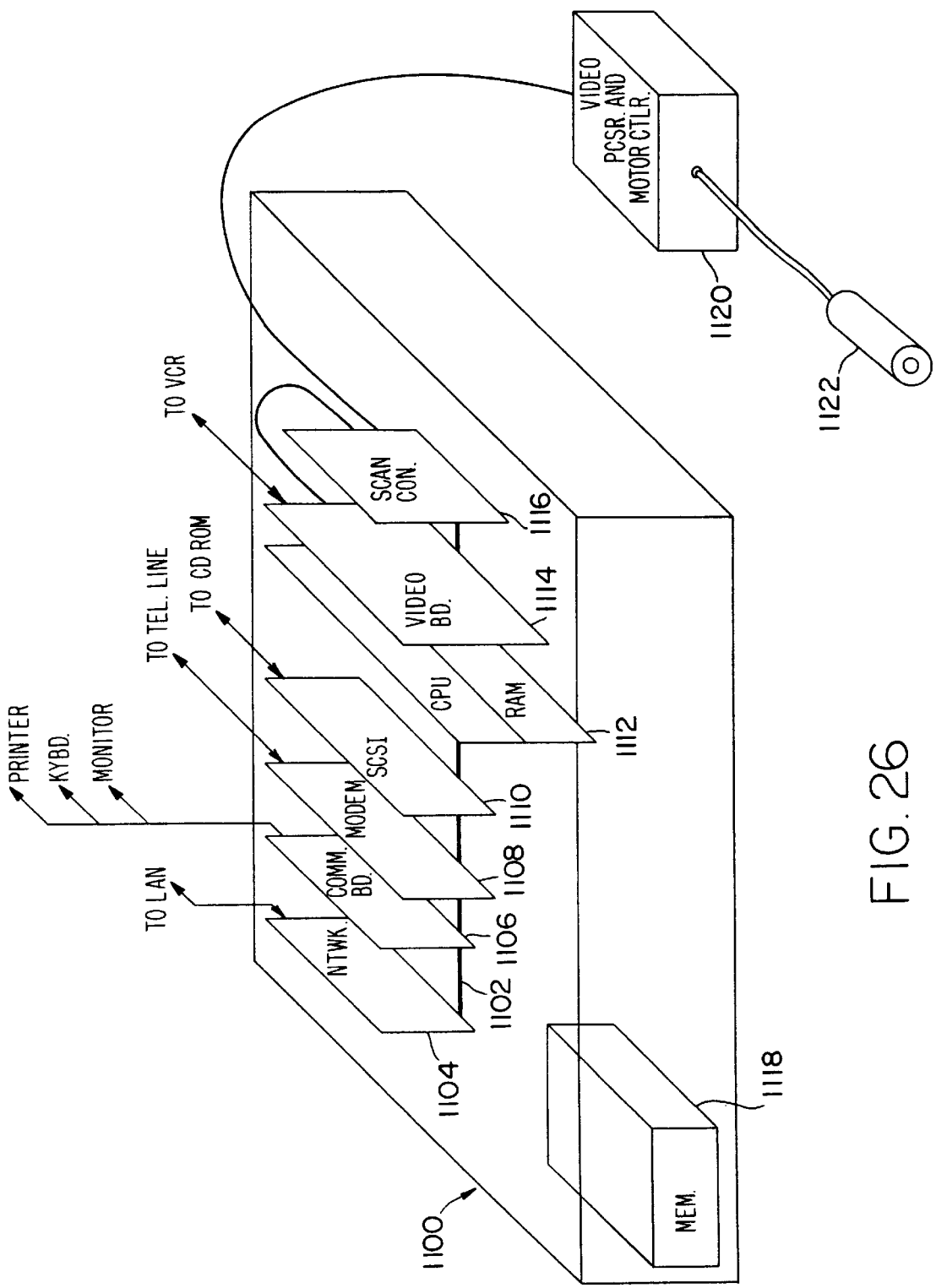
FIG. 26 diagrammatically illustrates the PC based ultrasound machine with a plug-in scan converter board for the PC and a video processor and motor controller unit as an external unit.

FIG. 26 diagrammatically illustrates a block diagram of the PC based ultrasound system 1100. This system includes a PC case which encloses various plug-in type PC boards. For example, the illustrated system includes a network board 1104 which connects to a local area network or LAN, a communications board 1102 linked to common peripheral equipment such as printers, keyboards and monitors, a modem 1108, a SCSI board 1110 connected to a CDROM player, a mother board 1112 with a CPU and a RAM, a video board 1114, and a scan conversion board 1116. In the illustrated embodiment, the video board is a Matrox MARVEL II realtime MPEG audio and video decoding board. This video board provides live video in a window on the screen, analog to digital conversion of the video images, realtime frame capture and processing and a digital video expansion bus. Also, the PC system includes conventional memory units 1118 which include removable floppy disc drives, hard drives and possibly removable tape drives.

The virtual control user interface controls the plug-in video board in a manner that is conventional. However, it is unique to the present invention to process an ultrasonic video image by the video board in conjunction with virtual user controls. For example, commercially available video boards can rotate a video image without significant difficulty. However, rotation of an ultrasound video image under the control of a virtual control user interface with a commercially available video board is unique. The integration of commercially available, plug-in, PC based components permits a much greater flexibility to the user and operator.

The scan converter board is connected to the video board by a cable which carries the standard formatted video signal partially processed by the video processors in external unit 1120 (discussed later) and the scan converter board (also discussed later). The video board 1114 may be connected to a video display monitor (not shown). Alternatively or in addition thereto, the video board 1114 is connected to a video player and recorder (a VCR). This connection permits the user to record and play back ultrasonic scans. With the playback feature, the user can post-process the ultrasound video image. This post processing is important if the video signal and resulting data may be shared between physicians, particularly experts in their fields. By permitting easy post-processing of the video image and potential capturing of the post processed image on the CDROM or the hard disc, the user can electronically ship the image to a specialist, have the specialist post-process the image or images, and then receive the post-processed image back into the ultrasound machine. This post-processed image can then be stored as a protocol to be later called up by the user during subsequent ultrasonic scans of the same or different patients. The use of an off-the shelf, commercially available video board to pre and post scan process the ultrasonic image enables the electronic image to be stored in a commercially recognized format, be electronically transmitted subsequently processed and returned to the originator without significant difficulties.

In addition to the PC encased components, the present embodiment of the system includes a video processor and motor controller device or unit 1120. Unit 1120 is connected to the scan converter. The video processor and motor controller drives and pre-processes raw scan video signals from the probe or scan head 1122. In another embodiment, the video processor and motor control unit 1120 will be encased within the PC box.

If the owner of the present ultrasound system wants to upgrade the system, he or she can use telephone lines to upgrade the control software, to upgrade the protocols for standard or customary ultrasonic scans, or simply remove and replace one or more boards in the PC case. Boards 1104, 1106, 1108, 1110, 1112, 1114 and 1116 are all plugged into the PC's main communications and control bus 1102.

Figure 27:
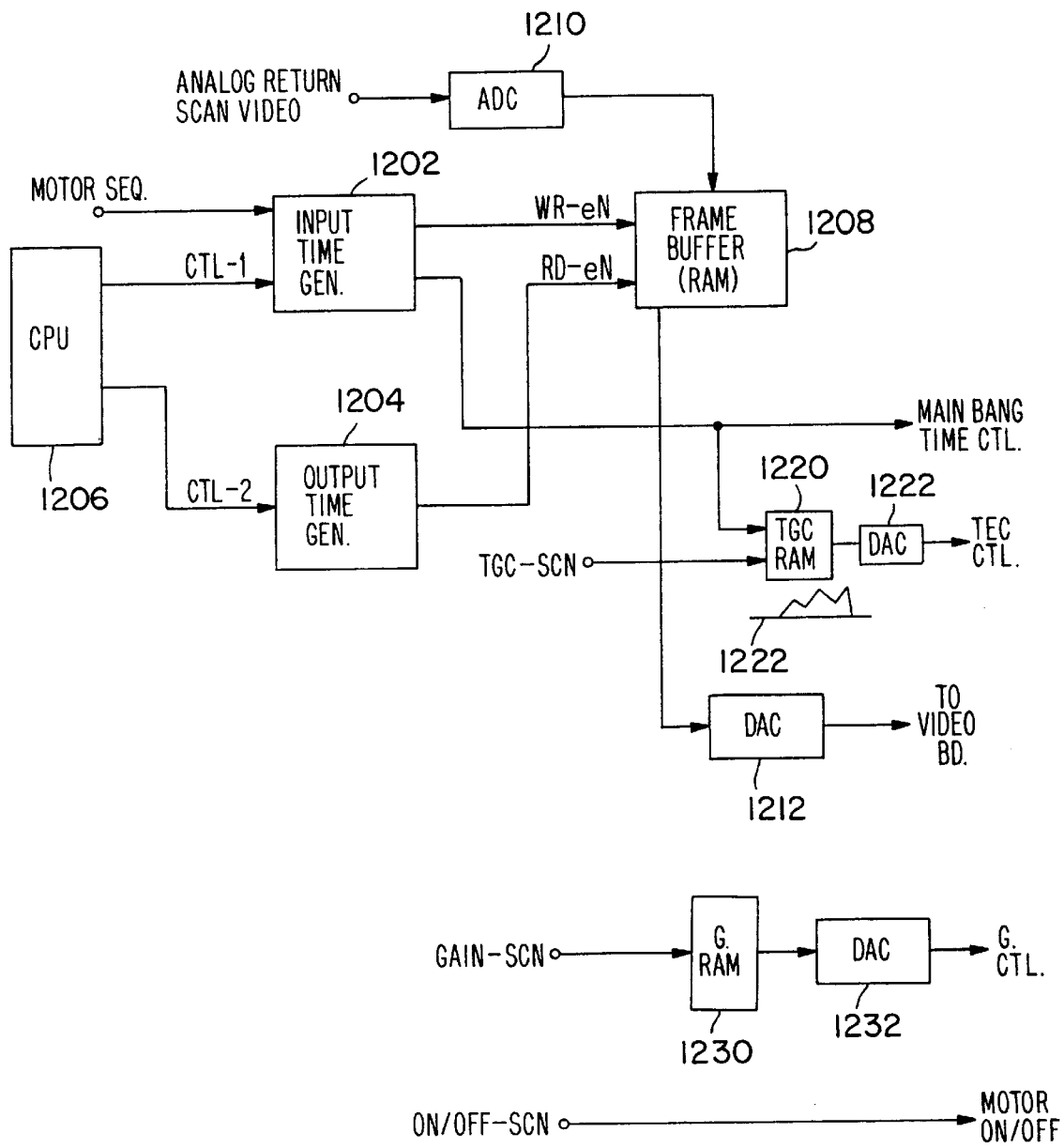
FIG. 27 diagrammatically illustrates a block diagram of the scan converter board; and, FIG. 28 diagrammatically illustrates the video processing and motor control unit for one embodiment of the present invention.

FIG. 27 diagrammatically illustrates the scan converter board. Scan converter board includes an input timing generator 1202 and an output timing generator 1204. CPU or central processing unit 1206 may be on the video scan board or the main CPU could be utilized to generate control CTL-1 and control CTL-2 signals to timing generators 1202 and 1204. The input timing generator 1202 develops a write enable signal WR-EN for a frame buffer 1208. Output timing generator 1204 generates a read enable RD-EN for frame buffer 1208. In addition, the analog return scan video signal is applied to an analog to digital converter ADC 1210. The digital representation of the scan video is applied to the input of frame buffer 1208. Frame buffer 1208 is a memory device which captures a significant portion of the scan video output by the scan head. The frame buffer formats the raw video signal into a common video format.

The output of the frame buffer 1208 is applied to the digital to analog converter DAC 1212. The analog version of the resulting signal is feed to the video board shown in FIG. 26.

In addition to the write enable signal for the frame buffer 1208, the input timing generator 1202 develops a main bang timing control signal which is applied to the video processor and motor control unit. This main bang time control signal provides a timing signal to release the voltage burst which activates the transducer in the scan head to develop the ultrasound signal. After the sound wave is generated, the transducer is monitored and begin receiving the echo. This echo is, after some processing by the video processing unit, applied as analog return scan video into ADC 1210.

In addition, the scan converter board includes a timing gain control or TGC RAM unit 1220. The main bang time control signal is applied to the TGC RAM 1220. In addition, the virtual user control software applies a TGC-screen (TGC-SCN) signal to TGC RAM 1220. The TGC RAM 1220 can develop a ramp, a wave, or other type of gain control based upon the TGC-SCN signal developed by the virtual control user interface. The signal identified as 1222 shows one type of TGC control signal. The output of TGC RAM 1220 is applied to a digital to analog converter DAC 1222. The output, in analog form, is the TGC control which is fed to the video processor and motor control unit.

In addition to the forgoing, the scan converter board includes a timing gain RAM 1230 which receives as an input from the virtual control user interface software a gain/screen command gain-SCN. The output of gain RAM 1230 is applied to a digital to analog converter DAC 1232. The analog version of that overall gain control G-CTL is applied to the video processor and motor control unit. Additionally, the virtual user control develops an on/off screen command which is applied as a motor on/off signal.

The TGC RAM 1220 must be timed to the main bang time control signal because the TGC control is utilized to increase the gain in the video processor unit based upon the time of receipt of the waves of echo indicating different depths in the ultrasound scan field.

The frame buffer RAM 1208 accepts only a certain portion of the scan video based upon the write enable signal from input timing generator 1202. The frame buffer 1208 must accept only a part of the scan video because only a portion of that video signal is actually representative of the ultrasound scan. In other words, the return echo from the scan head includes all the output data from the transducer in the scan head. Only a small portion of the transducer's output data is truly representative of received ultrasonic echo signals. For example, a scan head that utilizes a rotating mirror will only generate "appropriate" ultrasonic echo data signals during a certain accurate swing of the mirror. The write enable control captures this arcuate swing data.

Further, the frame buffer 1208 outputs video information based upon the read enable control from output timing generator 1204. The Frame Buffer Table set forth below gives an example of such an operation. In the Frame Buffer Table, lines 4-48 are captured by frame buffer 1208. Upon receipt of the read enable command from timing generator 1204, frame buffer 1208 outputs video signals in a standard video format (e.g., 262 lines per field) to DAC 1212. In other words, a video conversion is made in frame buffer 1208. Alternatively, the read enable signal can be utilized to output only a small portion of the captured scan video signal.

| Frame Buffer Table | | |
|---|---|---|
| Input Line | WR-EN | RD-EN |
| 1-1 | 0 | |
| 2 | 0 | |
| 3 | 0 | |
| 4 | 1 | Converts L4–L48 to 262 lines per field |
| . | . | |
| . | . | |
| . | . | |
| 45 | 1 | |
| 46 | 1 | |
| 47 | 1 | |
| 48 | 1 | |
| 49 | 0 | |
| 50 | 0 | |
| . | . | |
| . | . | |
| . | . | |
| 358 | 0 | |
| 359 | 0 | |
| 360 | 0 | |
| 1-2 | 0 | |
| 2-2 | 0 | |
| 3-2 | 0 | |
| 4-2 | 0 | |
| 5-2 | 1 | |
| 6-2 | 1 | |

Since only a portion of the raw scan video is utilize it is necessary to identify the position of the motor rotating the mirror or the transducers in the scan head. A motor sequence signal is input into input timing generator 1202. This motor sequence signal is obtained from a transducer attached to the motor in the scan head. Accordingly, the input timing generator 1202 has some indication where the motor is located or when a certain portion of the motor has passed a pre-determined point. This provides a timing sequence to trigger the input timing generator.

Figure 28:
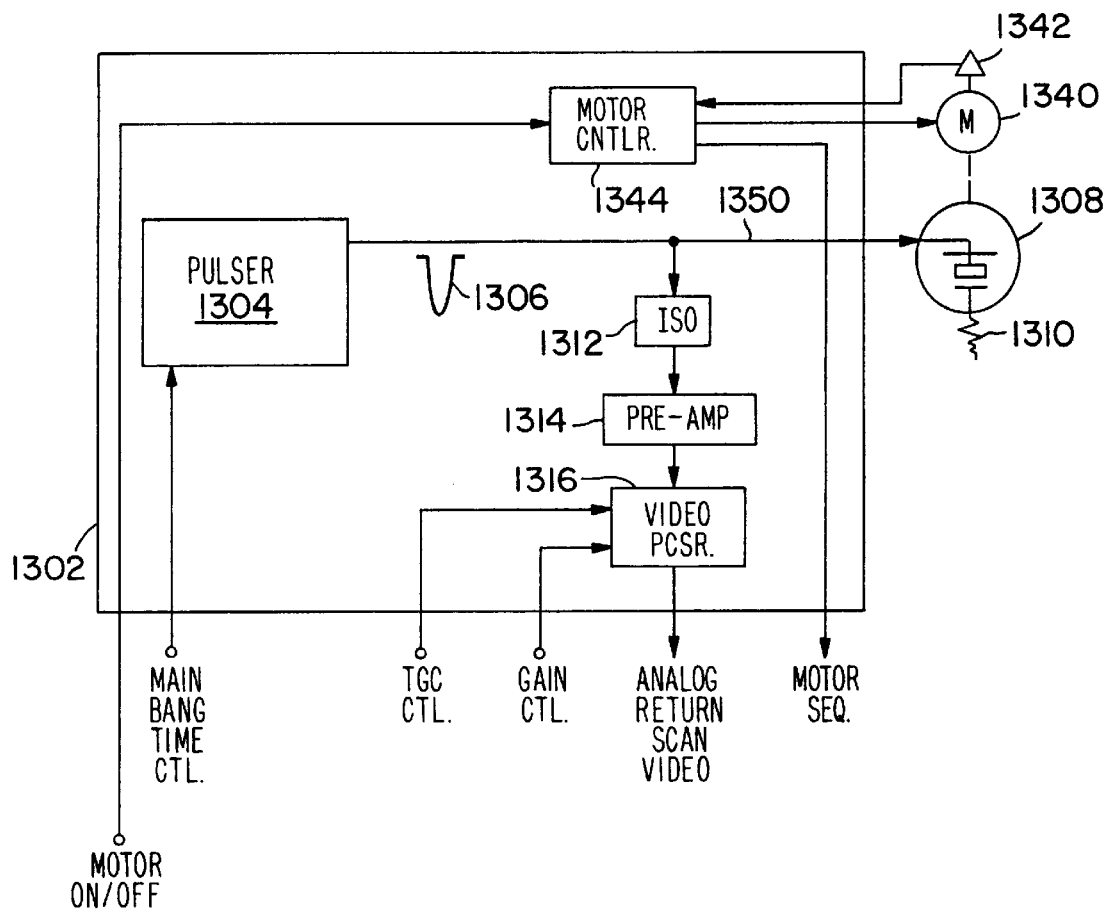

FIG. 28 diagrammatically illustrates the video processor and motor controller unit. The scan converter board delivers main bang time control signals, TGC control signals and gain control signals to video processor and motor control unit 1302. The main bang time control signal is a timing pulse that is applied to pulser 1304. Pulser 1304 develops a significant but short voltage or current pulse identified by signal 1306. This signal is applied to the transducer in the scanhead. The transducer is diagrammatically illustrated in this figure as transducer 1308. The transducer generates a sonic pulse diagrammatically illustrated as pulse 1310.

Since the transducer is also a receiver, pulse 1310 also represents the received echo from that ultrasonic ping. Therefore, transducer 1308 upon receipt of the echo 1310, develops an electrical representation of that echo. An isolation circuit 1312 isolates the driving voltage pulse 1306 and passes the received echo representation to pre-amplifier 1314. The output of pre-amplifier 1314 is passed to video processor 1316. Video processor 1316 also receives the analog versions of timing gain control TGC-CTL and gain control CTL signals from the scan converter. The video processor 1316 outputs the analog return scan video which is applied to the A to D converter ADC 1210 in the scan converter board.

The moveable portions in the scan head, either the mirror or the transducer, are driven by a motor 1340. A tachometer or position sensor 1342 is attached to the shaft of motor 1340. The output of the position sensor and the control signal to drive motor 1340 is generated by motor control 1344. Motor controller 1344 obtains the motor on/off signal from the scan converter board. The signal from position sensor 1342 is conditioned by motor control circuit 1344 and its output is designated as motor sequence data applied to the input timing generator 1202 in the scan converter.

Isolation circuit 1312 could be any type of isolation circuit which filters or limits the significant drive voltage and separates the return ultrasonic data signals on line 1350 from pre-amplifier 1314 and video processor 1316.

In operation, the video processor 1316 is a series of variable gain amplifiers that are controlled based upon the analog TGC control signals and gain control signals developed by the scan converter.

Pulser 1304 is a series of amplifiers and timing chips which are activated upon receipt of the main bang time control signal. The output of pulser 1304, that is, the exemplary voltage pulse 1306, drives the transducer 1308 in the scan head.

The claims appended hereto are meant to cover modifications and changes within the spirit and scope of the present invention.

What is claimed is:

1. An ultrasound device with a virtual control user interface electronically couple to an ultrasound scan head comprising:

a display monitor;

a keyboard;

a personal computer data and communications bus;

a central processing unit (CPU), a memory unit, and an input/output interface for said display monitor and said keyboard, all physically and electronically plugged into said bus;

a scan head converter and driver coupled between said bus and said ultrasound scan head;

a virtual control user interface including a software driven display, obtained from memory and displayed on said display monitor under the control of said CPU, revealing images representative of a hardware control configuration for another ultrasound processor;

said images including:

a plurality of gain control tactile user interfaces, a plurality of ultrasound image enhancement control tactile user interfaces, and, at least one focus control tactile user interface, said software driven display having multiple menu levels for display of said plurality of gain control images, said plurality of ultrasound image enhancement control images and said focus control image, said software driven display further configured to reveal images of more than one ultrasound processor; and, means for controlling said scan head based upon said virtual control user interface and for processing scan head data signals.

* * * * *